(12) United States Patent
Giaya et al.

(10) Patent No.: US 11,266,373 B2
(45) Date of Patent: Mar. 8, 2022

(54) DEVICES AND METHODS FOR MEASURING VASCULAR DEFICIENCY

(71) Applicants: Worcester Polytechnic Institute, Worcester, MA (US); University of Massachusetts, Boston, MA (US)

(72) Inventors: Dennis Giaya, Woods Hole, MA (US); Rebecca Stolarczyk, Waltham, MA (US); Yitzhak Mendelson, Worcester, MA (US); Arriyan Samandar Dowlatshahi, Worcester, MA (US); Raymond Dunn, Shrewsbury, MA (US)

(73) Assignees: University of Massachusetts, Boston, MA (US); Worcester Polytechnic Institute, Worcester, MA (US)

( * ) Notice: Subject to any disclaimer, the term of this patent is extended or adjusted under 35 U.S.C. 154(b) by 566 days.

(21) Appl. No.: 15/488,364

(22) Filed: Apr. 14, 2017

(65) Prior Publication Data
US 2017/0296139 A1    Oct. 19, 2017

Related U.S. Application Data

(60) Provisional application No. 62/482,007, filed on Apr. 5, 2017, provisional application No. 62/323,073, filed on Apr. 15, 2016.

(51) Int. Cl.
*A61B 8/06* (2006.01)
*A61B 8/00* (2006.01)
(Continued)

(52) U.S. Cl.
CPC .............. *A61B 8/06* (2013.01); *A61B 5/0022* (2013.01); *A61B 5/0084* (2013.01); *A61B 5/01* (2013.01);
(Continued)

(58) Field of Classification Search
CPC ....... A61B 5/0022; A61B 5/0084; A61B 5/01; A61B 5/02007; A61B 5/02055;
(Continued)

(56) References Cited

U.S. PATENT DOCUMENTS 5,260,557 A * 11/1993 Kissh ................... G01S 3/7867
250/203.6
9,314,225 B2    4/2016 Steen et al.
(Continued)

OTHER PUBLICATIONS

Chao et al. "Current Approaches to Free Flap Monitoring" www.psnjounalonline.com vol. 34, No. 2, Apr.-Jun. 2014 (Year: 2014).*
(Continued)

*Primary Examiner* — Michael T Rozanski
(74) *Attorney, Agent, or Firm* — McCarter & English, LLP

(57) ABSTRACT

The present invention relates to devices and methods for measuring vascular deficiency using Doppler ultrasound detection. Embodiments can be used to monitor the condition of surgical tissue flaps or other conditions in which obstruction in the vascular system can impact patient health. The systems can include a Doppler ultrasound probe, a color probe, a temperature probe, and/or other suitable probes to measure blood volume and perfusion status of a tissue region. The systems and methods can be used to monitor flaps after flap transplant surgeries. The systems and methods can automatedly assess tissue condition and alert the patient or medical staff if the condition has fallen below a threshold indicating occlusion of a blood vessel. One or more additional sensors can be integrated into a probe to measure vascular conditions and a metric can be computed based on sensed data.

35 Claims, 32 Drawing Sheets

(51) Int. Cl.

| | |
|---|---|
| *A61B 5/026* | (2006.01) |
| *G01S 15/89* | (2006.01) |
| *A61B 5/055* | (2006.01) |
| *G01S 7/52* | (2006.01) |
| *A61B 5/01* | (2006.01) |
| *A61B 5/0205* | (2006.01) |
| *A61B 5/00* | (2006.01) |
| *A61B 8/08* | (2006.01) |
| *A61B 8/12* | (2006.01) |
| *A61B 5/02* | (2006.01) |
| *G16H 40/67* | (2018.01) |
| *G16Z 99/00* | (2019.01) |
| *A61B 5/024* | (2006.01) |
| *A61B 5/022* | (2006.01) |

(52) U.S. Cl.
CPC .......... *A61B 5/026* (2013.01); *A61B 5/02007* (2013.01); *A61B 5/02055* (2013.01); *A61B 5/0261* (2013.01); *A61B 8/0883* (2013.01); *A61B 8/0891* (2013.01); *A61B 8/12* (2013.01); *A61B 8/4455* (2013.01); *A61B 8/463* (2013.01); *A61B 8/488* (2013.01); *A61B 8/5223* (2013.01); *G16H 40/67* (2018.01); *G16Z 99/00* (2019.02); *A61B 5/022* (2013.01); *A61B 5/02416* (2013.01); *A61B 5/055* (2013.01); *A61B 5/4244* (2013.01); *A61B 5/445* (2013.01); *A61B 5/6847* (2013.01); *A61B 8/4494* (2013.01); *A61B 8/461* (2013.01); *G01S 7/52023* (2013.01); *G01S 15/8979* (2013.01)

(58) Field of Classification Search
CPC ..... A61B 5/022; A61B 5/02416; A61B 5/026; A61B 5/0261; A61B 5/055; A61B 5/4244; A61B 5/445; A61B 5/6847; A61B 8/06; A61B 8/0883; A61B 8/0891; A61B 8/12; A61B 8/4455; A61B 8/4494; A61B 8/461; A61B 8/463; A61B 8/488; A61B 8/5223; G01S 15/8979; G01S 7/52023; G06F 19/00; G16H 40/67
See application file for complete search history.

(56) References Cited

U.S. PATENT DOCUMENTS

| | | | | |
|---|---|---|---|---|
| 2005/0014995 | A1* | 1/2005 | Amundson | ............ A61B 1/018 600/105 |
| 2005/0165310 | A1 | 7/2005 | Bindefeld | |
| 2006/0100530 | A1 | 5/2006 | Kliot et al. | |
| 2007/0213616 | A1* | 9/2007 | Anderson | ............ A61B 8/0833 600/448 |
| 2011/0098564 | A1 | 4/2011 | Larson et al. | |
| 2015/0094593 | A1 | 4/2015 | Machan et al. | |
| 2015/0198797 | A1 | 7/2015 | Andre et al. | |
| 2015/0202020 | A1* | 7/2015 | Fisher | .................... A61N 1/059 600/424 |
| 2016/0022223 | A1* | 1/2016 | Grundfest | ............ A61B 5/0062 600/324 |

OTHER PUBLICATIONS

Frost et al., Direct comparison of postoperative monitoring of free flaps with microdialysis, implantable cook-swartz Doppler probe, and clinical monitoring in 20 consecutive patients. Microsurgery. May 2015;35(4):262-71.

GE Healthcare, Vscan with Dual Probe, Indications Reference Guide. 1 page, (2014).

Giaya et al., Postoperative Telemonitoring of Flap Physiology in Microvascular Free Tissue Transfer. A Major Qualifying Project Report submitted to the faculty of Worcester Polytechnic Institute in partial fulfillment of the requirements for the degree of Bachelor of Science. 235 pages, Apr. 28, 2016.

Gornik et al., ACCF/ACR/AIUM/ASE/IAC/SCAI/SCVS/SIR/SVM/SVS/SVU 2013 Appropriate Use Criteria for Peripheral Vascular Ultrasound and Physiological Testing Part II: Testing for Venous Disease and Evaluation of Hemodialysis Access. Journal of the American College of Cardiology. Aug. 2013;62(7):650-65.

Huber et al., Popliteal vein compression under general anaesthesia. Eur J Vasc Endovasc Surg. Apr. 2009;37(4):464-9.

Khalid et al., Color doppler ultrasonography is a reliable predictor of free tissue transfer outcomes in head and neck reconstruction. Otolaryngol Head Neck Surg. Apr. 2006;134(4):635-8.

Kimura et al., Diagnostic performance of a pocket-sized ultrasound device for quick-look cardiac imaging. Am J Emerg Med. Jan. 2012;30(1):32-6.

Nakanishi et al., Detection of Deep Venous Thrombosis Using a Pocket-Size Ultrasound Examination Device. JACC Cardiovasc Imaging. Jul. 2016;9(7):897-898.

Wells et al., Evaluation of D-dimer in the diagnosis of suspected deep-vein thrombosis. N Engl J Med. Sep. 25, 2003;349(13):1227-35.

Invitation to Pay Additional Fees for Application No. PCT/US2017/027789, dated Sep. 8, 2017, 10 pages.

International Search Report and Written Opinion for Application No. PCT/US2017/027789, dated Nov. 17, 2017, 15 pages.

\* cited by examiner

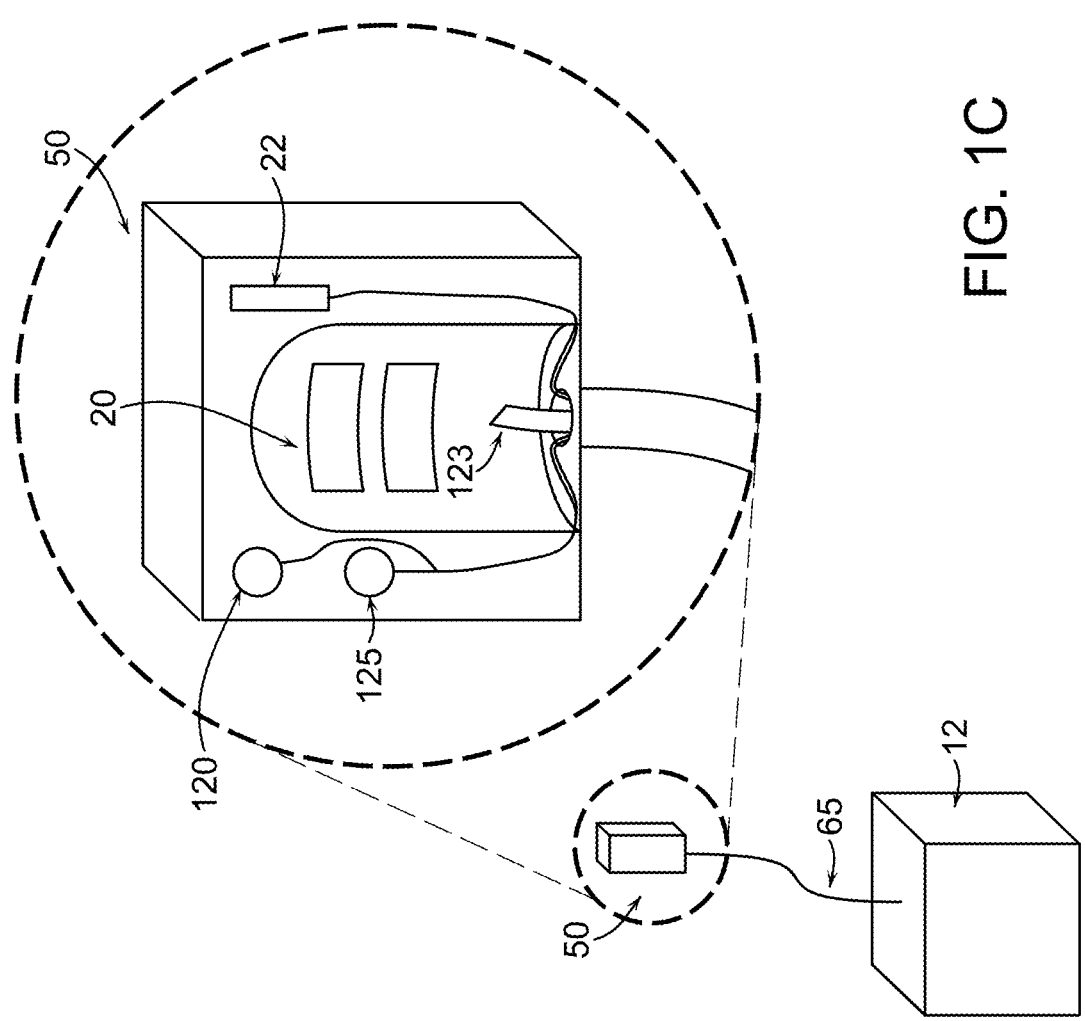
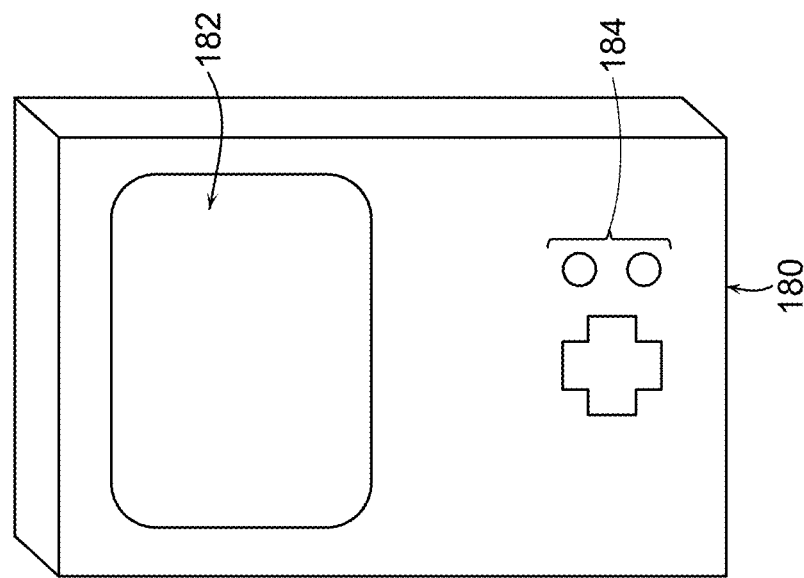
FIG. 1C

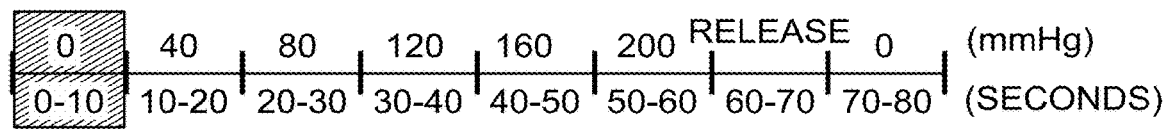
SUBJECT RADIAL POWER SIGNAL BEFORE INFLATION
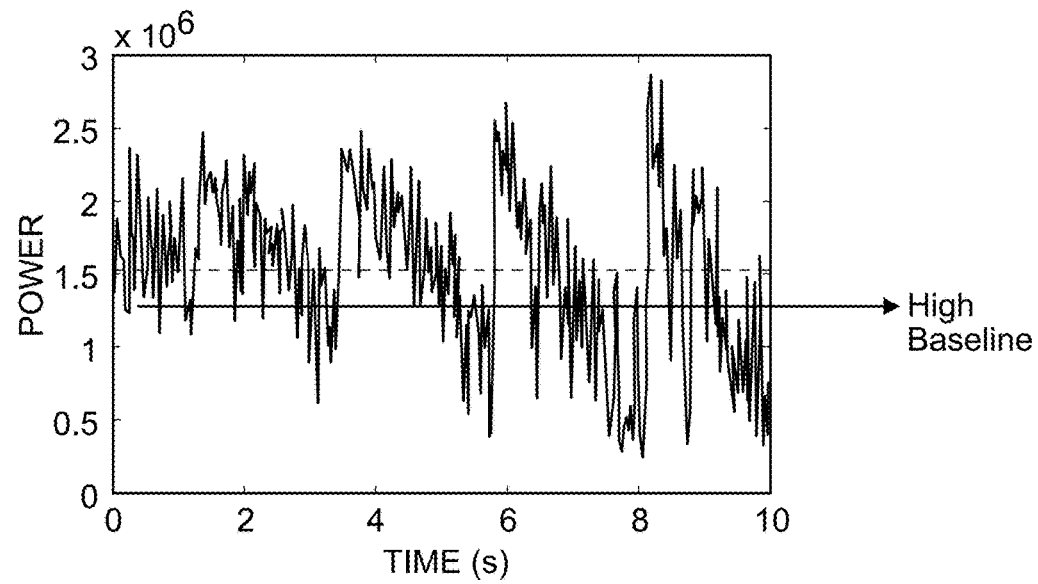
FIG. 6
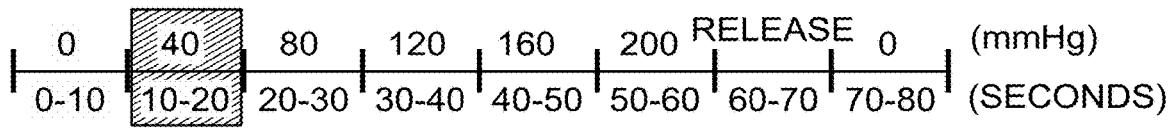
SUBJECT RADIAL POWER SIGNAL 40mmHg
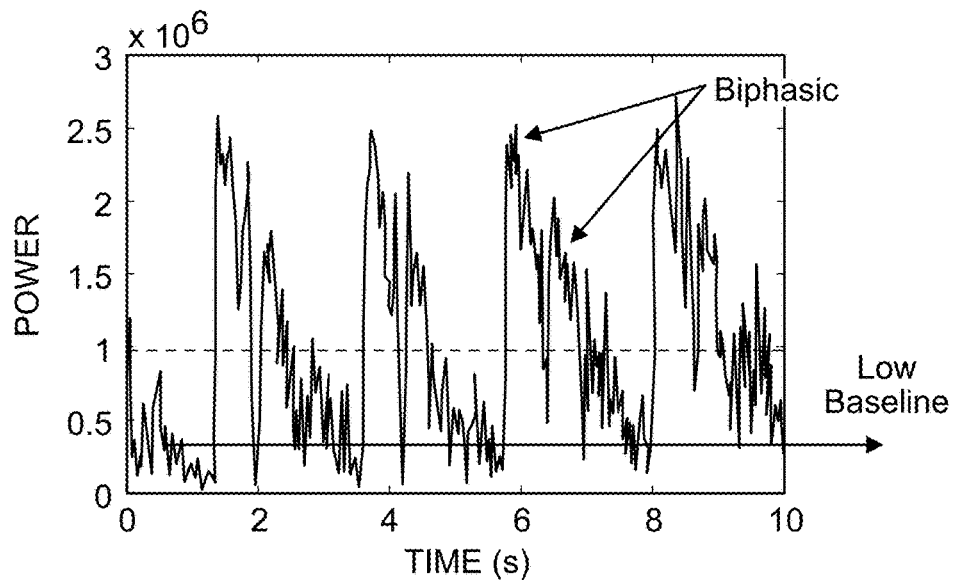
FIG. 7

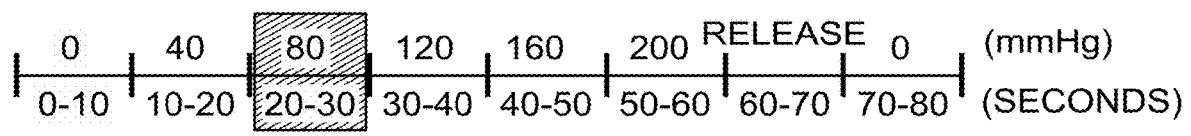
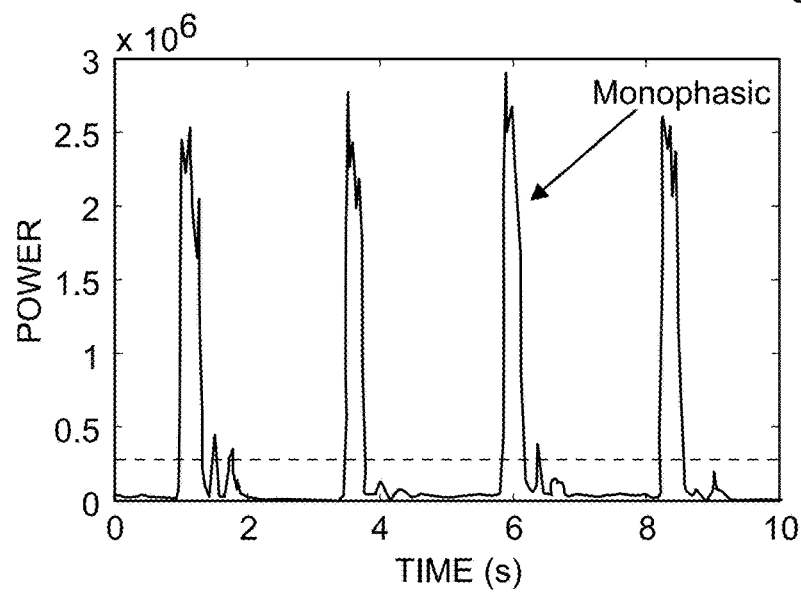
FIG. 8
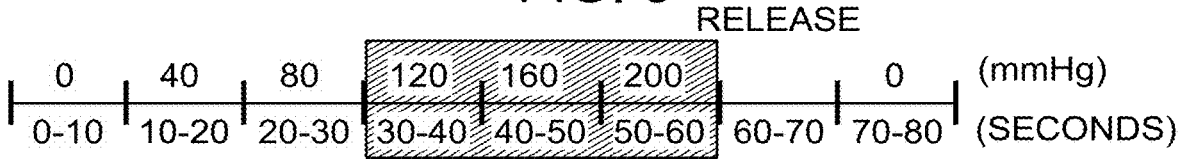
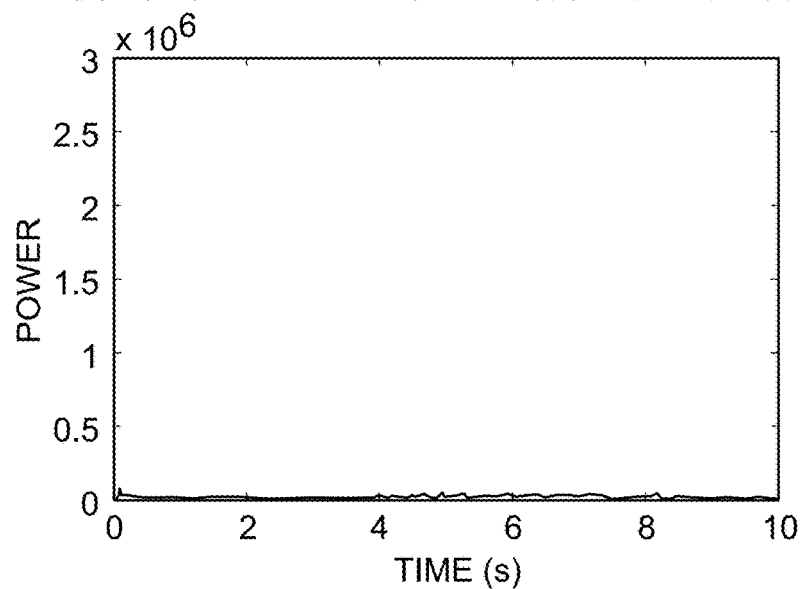
FIG. 9

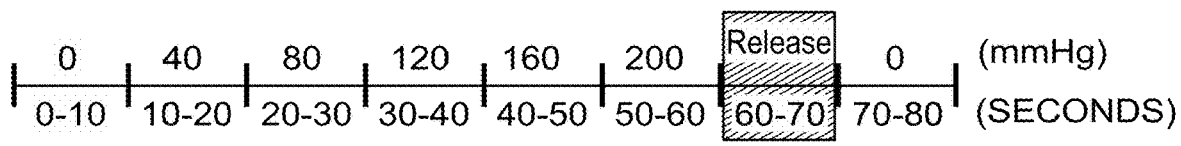
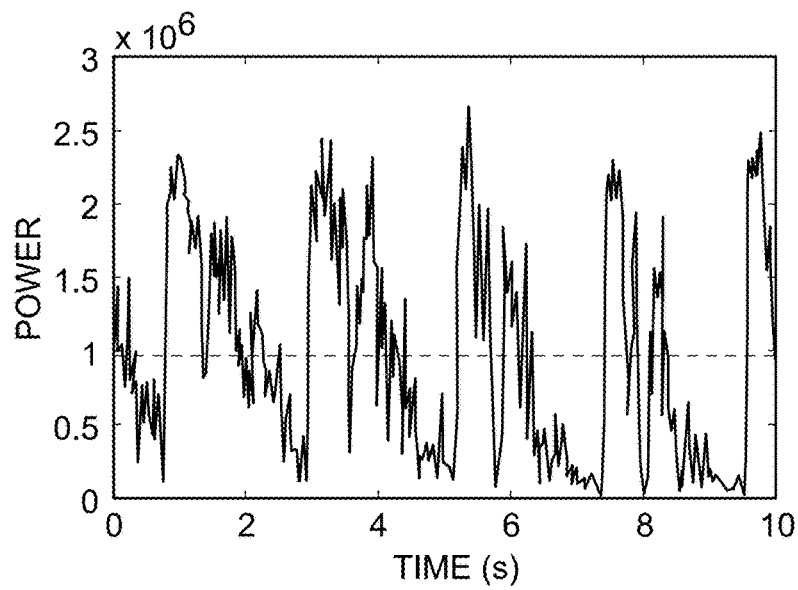
FIG. 10
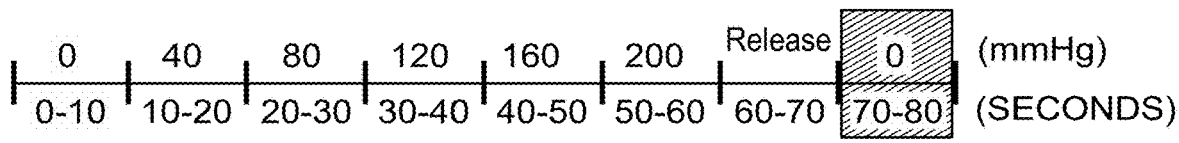
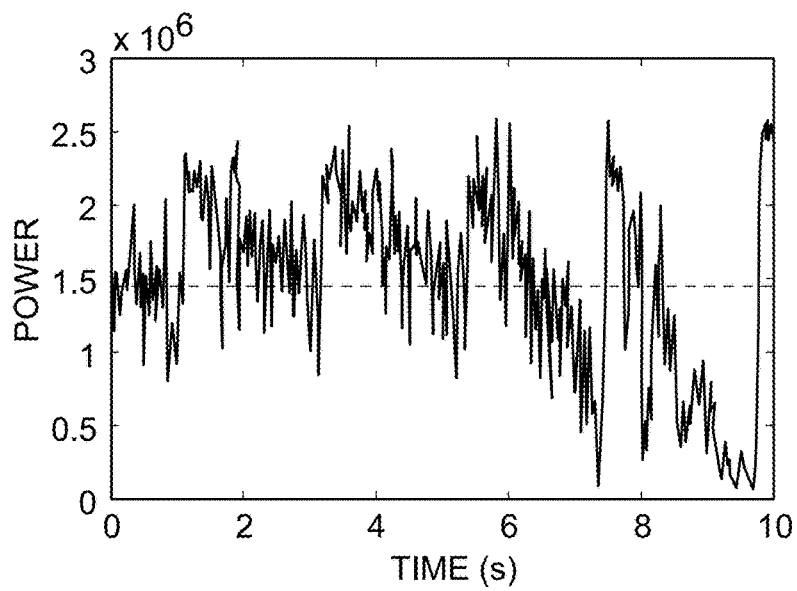
FIG. 11

Healthy Subject

Postoperative Patient

- Temperature
  - Venous compromise: 1°C differential between flap and reference
  - Arterial compromise: 3°C differential between flap and reference
- Doppler ultrasound
  - Venous compromise: loss of baseline signal
  - Arterial compromise: loss of biphasic signal

| Dashboard | HOME | PATIENTS | DEVICES | | Account |
|---|---|---|---|---|---|

| Patients |
|---|
| Patient 1 |
| Overnight,Text |
| Patient 2 |
| Test,Patient |
| Patient 3 |
| Patient 4 |
| Add A Patient |

Patient Summary

| Patient Name | Temperature Monitoring Status | Doppler Monitoring Status | Last Doppler Recording |
|---|---|---|---|
| Patient 1 | Inactive | Inactive | No Recordings Found |
| Overnight,Text | Inactive | Inactive | 4530 minutes ago |
| Patient 2 | Inactive | Inactive | 7597 minutes ago |
| Test,Patient | Running | Stopped | 24177726 minutes ago |
| Patient 3 | Inactive | Inactive | 21370 minutes ago |
| Patient 4 | Inactive | Inactive | 7061 minutes ago |

FIG. 13

| Dashboard | HOME | PATIENTS | DEVICES | | Account |

Patients

- Patient 1
- Overnight, Text
- Patient 2
- Test, Patient
- Patient 3
- Patient 4
- Add A Patient

Patient Alerts

Test - Alert Message - Priority 0
Test - Alert Message - Priority 1
Test - Alert Message - Priority 2

Temperature Data

— Probe1, °C  — Probe2, °C  — - Probe3, °C  — - - Probe4, °C (Temperature °C vs. axis 0.0–0.8, y-axis 0.00, 0.25, 0.50, 0.75, 1.00)

Doppler Data

△  ▭━━● 0:00 🔊 ▭

Here is a listing of the timestamped Doppler files:

doppler-20151203095305.wav
doppler-20151203092312.wav
doppler-20151203092136.wav
doppler-20151203092028.wav
doppler-20151203091916.wav
doppler-2015-12-15.23:53:12.wav
doppler-2015-12-15.23:50:45.wav
doppler-2015-12-15.23:50:39.wav
doppler-2015-12-15.23:50:19.wav
doppler-2015-12-15.23:50:02.wav
doppler-2015-12-15.23:40:48.wav
doppler-2015-12-15.23:35:26.wav
doppler-2015-12-15.14:56:10.wav
doppler-2015-12-15.14:48:27.wav

FIG. 14

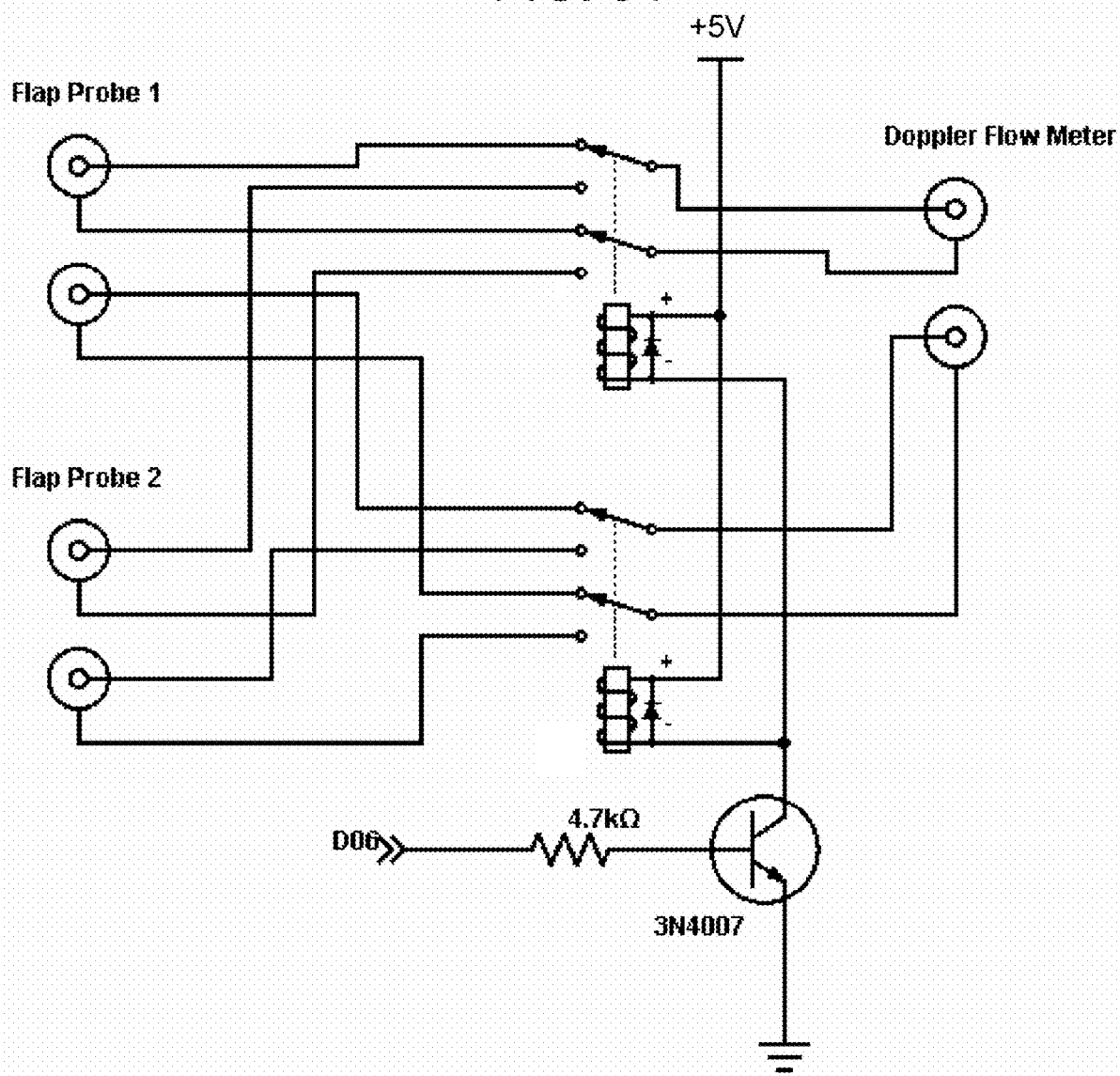

DEVICES AND METHODS FOR MEASURING VASCULAR DEFICIENCY

RELATED APPLICATIONS

This application claims priority to U.S. Provisional Application No. 62/323,073, filed Apr. 15, 2016, and U.S. Provisional Application No. 62/482,007, filed Apr. 5, 2017, the entire contents of both applications being incorporated herein by reference.

BACKGROUND

Surgical reconstructive procedures often involve a transplant of tissue to an afflicted region of a patient. Substantially planar tissue regions, such as skin and muscle tissue, are surgically attached as a so-called "flap" to the afflicted area for functional and/or aesthetic reconstruction. There are frequently circumstances where the vascular system in such tissue transfers is compromised and obstructions can occur that impact perfusion. More specifically Microvascular free tissue transfer is a type of reconstructive surgery in which a body part, organ, or flap is transplanted via detachment of blood vessels at the donor site and resuturing of vessels at the recipient site. The procedure, which is highly intensive and technically demanding, can be performed as a means of either aesthetic or functional reconstruction. Despite the relatively high success rate of free tissue transfer, failure due to late detection of postoperative complications can occur approximately 5% of the time, for example.

Issues that arise and persist for an extended period of time while the patient is recovering can ultimately lead to flap failure, in which the tissue dies and is no longer viable. Blood clot formation is a common complication, occurring in 10-12% of all free flap transplantations. The risk of thrombosis is highest immediately after surgery and can lead to tissue death if left untreated. In order to detect blood clot formation as soon as possible, patients are carefully monitored in the intensive care unit (ICU) for the first 72 hours after surgery. During this time, a nurse performs frequent examinations to evaluate the patient's status and check for signs of flap failure. The color, turgor, and temperature of the transplanted flap are manually determined by the nurse and assessed for abnormalities. Capillary refill and prick tests are also performed to evaluate blood flow to and from the tissue. In the instance of any physiological irregularities, the nurse alerts the surgeon who in turn provides the patient with the necessary treatment or returns the patient to the operating room to correct the issue.

There is a continuing need for improvements in detecting vascular obstructions and other conditions, particularly those arising in tissue transfer procedures, for example.

SUMMARY

The present invention relates to devices and methods for measuring vascular obstructions to improve detection, diagnosis and treatment of pathologies that can arise from such obstructions. Microvascular free tissue transfer, for example, involves transplantation of a tissue flap or section from one body region to another. During such a procedure, it is important that the transplanted tissue receive sufficient blood supply in order to ensure proper integration and healing of the transplanted tissue. Microvascular free tissue transfer employs vascular anastomosis, a surgical technique in which two blood vessels are connected via suturing of the two open ends. In free tissue transfer, the artery and vein of the transplanted flap is anastomosed to the vessels at the recipient site. Close monitoring of the surgical site is performed to identify signs of flap failure, such as resulting from thrombosis or hematoma.

Configurations herein are based, in part, on the observation that flap failure is preventable by rapid intervention at the early signs of failure. Unfortunately, conventional approaches suffer from the shortcoming that adequate monitoring is subject to temporal and evaluative variances. In other words, the frequency and qualitative interpretation of post-surgical examination can vary in determination of a failing flap, due in part to the overhead and expense incurred by a chosen manner of post-surgical monitoring.

Accordingly, configurations herein substantially overcome the above-described shortcomings of conventional approaches by providing a method of post-surgical monitoring and diagnosis for microvascular free tissue transfer procedures by affixing a plurality of probes at a surgical site for gathering physiological parameters indicative of a failure of a transplant flap, and receiving, by an interface to monitoring logic responsive to the epidermal probes, the gathered physiological parameters. Postoperative logic circuits and software analyzes, in an automated, iterative manner, the received physiological parameters for determining when a set of the received physiological parameters are indicative of a failing transplant flap, and renders the results of the analysis to a graphical user interface for remedial surgical attention. The automated and constant monitoring avoids extended intervals where an unmonitored physiological parameter could result in delayed remedial treatment. The probe can be attached to an epidermal surface of the skin of a patient, by suturing, with an adhesive, or in conjunction with a wound dressing such as a negative pressure wound therapy device in which suction is applied to the wound to remove fluids.

In the example configuration, analyzing further includes determining blood flow for detecting flap perfusion. Initially, the flap is perfused through the pedicle vessel until endothelialization is complete after the first two weeks. As a result, risk of flap compromise is greatest immediately after surgery when there is a sole means of perfusion for the newly transplanted tissue. Analyzing may also include comparing a temperature of the transplant flap with proximate tissue for detecting a temperature differential for detecting a significant difference (e.g. greater than 2° C.) indicating possible failure. The example configuration employs probes or sensors including a Doppler probe and thermistor, however other physiological parameters and sensor types may be employed, as disclosed further below.

The Doppler data can be processed with a data processor or other logic circuits to provide a quantitative characteristic, or metric, that represents the viability of the vascular tissue being measured. A preferred embodiment measures Doppler data at a plurality of different frequency bands at a plurality of time intervals during a monitoring period. Thus, a simple ultrasound Doppler system can provide a clear measurement of the state of blood flow over short periods or longer monitoring periods. This can be combined with light measurements of blood volume or pulsatile blood volume and temperature to compute a perfusion metric.

Another condition arising from vascular obstruction is deep vein thrombosis (DVT). Clots may form in the lower extremities of the vascular system due to a variety of conditions that cause coagulation of blood. Such clots or portions thereof may then release and travel to a lung, for example, causing a pulmonary embolism (PE). This can be a life threatening condition that has previously been diagnosed using ultrasound compression techniques in which a linear transducer images the arteries and veins in the legs of a patient. This typically requires an experienced sonographer to perform the study and a radiologist to review the study and provide a diagnosis. However, there are frequently circumstances where such resources are not readily available, and even when available, this procedure is time consuming, which can cause a significant delay in emergency treatment.

Embodiments of the present invention relate to systems and methods for detecting DVT in which a transducer probe as described herein in which transducer elements are measured to acquire Doppler data from the arteries and veins of a patient to aid in the fast diagnosis of vascular obstruction. Audio files and also be recorded to assist in the diagnosis. This can enable health care workers to obtain a preliminary diagnosis and initiate treatment, such as administration of an anticoagulant, until other techniques are available to confirm the diagnosis. The transducer probe can be of simple design using a pair of transducer elements, one for transmission and one for reception. This procedure can be conducted in a non-imaging mode where an emergency room physician can orient the probe at an angle such as 45 degrees relative to the vein being examined to record the required Doppler data.

Optionally, a plurality of pairs of transducer elements such as 8 or 16 can also be used. An alternative embodiment can utilize a low resolution image to aid in locating the vein to be examined. A Doppler imaging transducer can have 32 transducer elements or less formed into a linear or curved linear array, or preferably have from 4 to 16 transducer elements that provide a low resolution image of an arterial or venous obstruction and generate Doppler blood flow data to characterize the degree of obstruction. The transducer array can be mounted to a probe housing that can be attached to a tissue flap for monitoring as described herein. Alternatively, the transducer array can be mounted within a handheld probe housing that can be oriented at different angles relative to the artery and/or vein being scanned.

The transducer probe can be a handheld device that transmits data to a portable handheld display and processing device with a cable or by wireless transmission. The transducer probe can be powered by cable or using a battery in the transducer probe. The transducer probe can also include transmit/receive circuitry and optionally can include a beamformer integrated circuit that can generate digital data. A data processor can also be mounted in the transducer probe to condition the data for wireless transmission using a wireless transceiver. The processor can be programmed to control transmission of pulsed or continuous wave energy into the tissue. Alternatively, the handheld display and processing unit can include one or more data processors or controllers to control probe operation and perform data processing and transmission of the data to a network as described herein. The handheld display and processing unit can comprise a wireless mobile device such as a mobile phone or tablet powered by a battery that can connect via a cellular network to a remote server for secure transmission of data to a data warehouse or other electronic storage media. The display can comprise a liquid crystal touchscreen display, for example, and can utilize a graphical user interface with a virtual keyboard and touch actuated icons used to control patient data entry and system operation. The display can present the frequency of probe operation and associate the spectral and power windows as described herein to determine monophasic, biphasic or triphasic characteristics of each vein being examined. The GUI can thus display the status of the iliac, femoral, popliteal, tibial and peroneal veins, for example. Thus, the system can determine if there is a total obstruction, a partial obstruction or no obstruction in each vein. The processor in the display housing is programmed to have adjustable thresholds that are applied to the recorded data to determine the degree of obstruction.

An experienced user of the system can also perform a partial compression analysis that is particularly useful in distinguishing no obstruction from a total obstruction, for example. The probe can be used to collect data while compression is applied to the suspected area of a thrombus.

The system can also be configured to portable mobile use wherein the probe is connected to a body-worn, battery powered processor housing by wired or wireless connection. This enables a patient to move outside of a hospital or clinic, while still being monitored remotely.

While the system and methods defined herein have been particularly shown and described with references to embodiments thereof, it will be understood by those skilled in the art that various changes in form and details may be made therein without departing from the scope of the invention encompassed by the appended claims.

BRIEF DESCRIPTION OF DRAWINGS

Various configurations depicting the above features and benefits as disclosed herein are shown and described in connection with the following figures:

FIG. 1C illustrates a schematic of a system for measuring vascular deficiency in accordance with various embodiments described herein;

FIGS. 6-9 illustrate filtered and processed radial power signal data derived from ultrasound measurements for increasing levels of applied pressure between 0 and 120 mmHg in accordance with embodiments described herein;

FIGS. 10 and 11 illustrate filtered and processed radial power signal data derived from ultrasound measurements upon pressure release and recovery, respectively, in accordance with embodiments described herein;

FIG. 13 illustrates an example graphical user interface for a patient summary page in accordance with embodiments described herein;

FIG. 14 illustrates an example graphical user interface for a patient monitoring page in accordance with embodiments described herein;

FIG. 34 illustrates a schematic for a probe multiplexer in accordance with embodiments described herein;

DETAILED DESCRIPTION

Figure 1A:
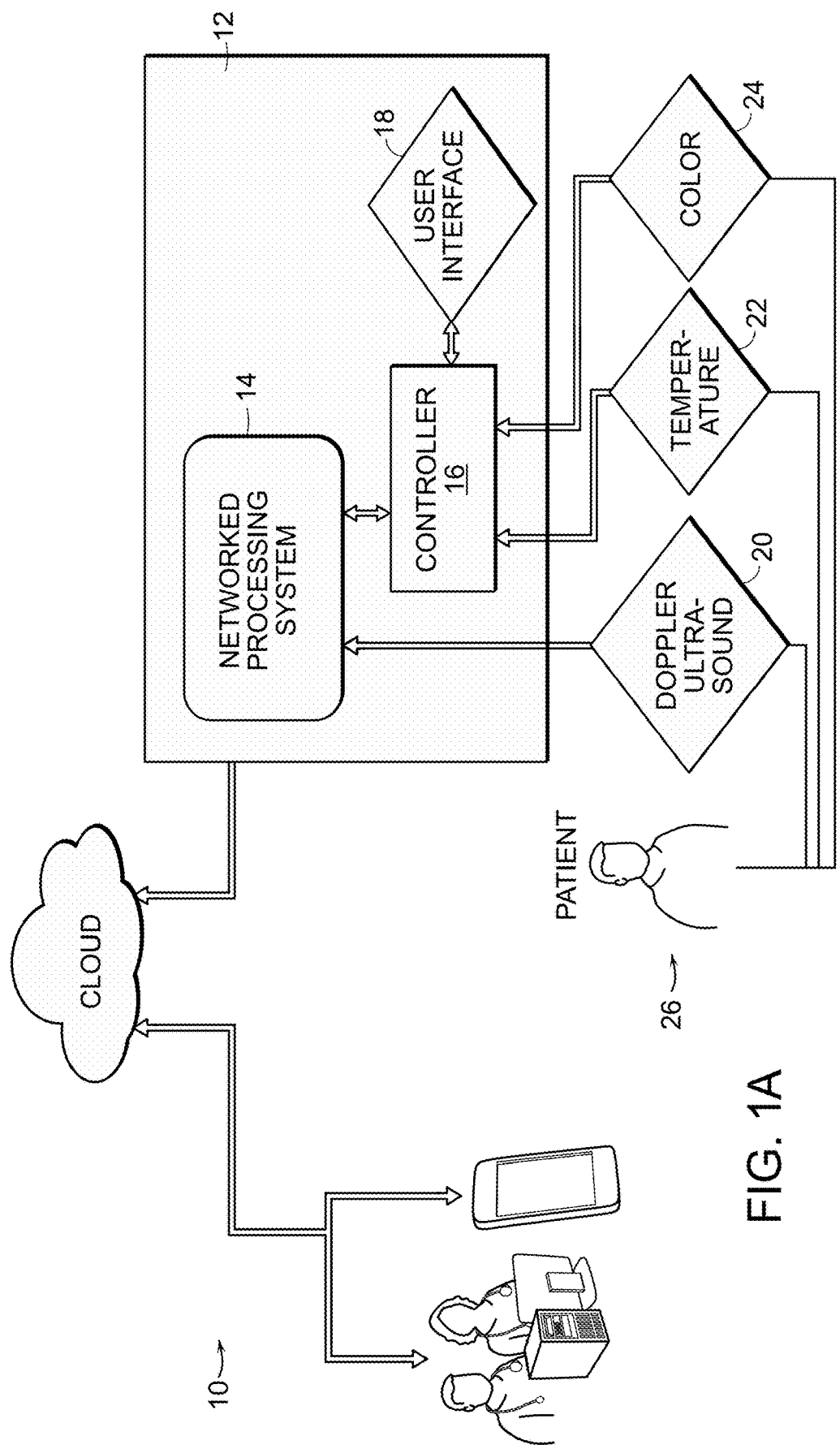
FIG. 1A illustrates a system for measuring vascular deficiency in a patient in accordance with embodiments of the invention.

Rapid and accurate detection of blood clot formation is critical to recovering tissue and preventing flap failure. Current methods for evaluating flap recovery are both delayed and subjective, relying solely on noninvasive examinations to identify complications occurring within the tissue. Because the physical symptoms of a blood clot may not appear immediately, a clinical evaluation may not detect an occlusion until after the tissue has begun to die.

Doppler ultrasound and color can be used to monitor for distress signs in order to wirelessly alert medical staff to the earliest signs of flap failure. The device is simple and harmless to the patient and free flap. The system displays or alerts relatively inexperienced personnel to the development of circulatory impairment.

The first main advantage is earlier detection. By monitoring the flap continuously, problems can be addressed as they occur. The current protocol at many hospitals is to monitor the patient every hour for the first twenty-four hours, followed by every two hours for the next 48 hours, and finally every four hours until discharge. Devices described herein can eliminate the time wasted between the onset of a problem and its detection due to infrequent sampling. The second major advantage of the device is an objective data. The subjectivity of the current practices leads to indecisive action because one person's judgment on the color of a compromised flap may be different from another person's. Human eyes and ears are not sensitive enough to pick up the subtle details that indicate early signs of flap compromise. Analysis of the data collected can objectively determine whether sufficient criteria have been met to indicate a definitive need for re-exploration of the flap. As such, if the device is successful and reliable in early detection of circulatory problems within flaps then it would no longer be necessary to send medical staff to the patient in order to perform monitoring. This frees up nursing staff to tend to other patients more often and also raises the potential of transferring the patient out of the ICU sooner. The frequency at which nurses must check the condition of the flap requires that the patient be in the ICU. Automating this process with our device could allow for the patient to be transferred to a general floor, which would significantly reduce costs. By satisfying both of these areas the device has potential to become the new gold standard in free flap monitoring.

The device can comprise three main stages that differ by function. First are the sensors that interface with the human body at the site of the flap to collect physiological data. The sensors interface with the second major portion of the device, the processor housing or body, which is where the data analysis and transmission occurs. The housing can include a controller board that interfaces with all of the sensors and provides analog to digital conversion for the signals. The controller can comprise an Arduino that communicates with a system processor such as a Raspberry Pi unit that processes the signals to determine whether criteria to raise an alarm have been met and also upload the information over the Internet to a secure MySQL database for access from the third stage of the device: the application. The web-based application enables surgeons to log in from any mobile device with internet access and view real time data for a patient.

The sensors and methods provide for unobtrusively attach them to the flap and recording for extended periods of time. The sensors are biocompatible, sensitive, and the ability to detect early signs of circulatory insufficiency. The primary challenge for the body of the device is to be able to automatically detect an insufficiency and initiate the process of alerting medical staff. This requires the sensors and framework for data acquisition to be operational so that real data can be acquired for analysis and development.

Microvascular free tissue transfer is a reconstructive surgical procedure in which a body part, an organ, or a piece of tissue is transplanted from one area of the body to another for surgical reconstructions, including those of the breast, head, and neck.

Procedures can be for cosmetic purposes, including postmastectomy breast reconstruction and facial reconstruction after burns or disfigurement. Conversely, functional reconstruction is needed in cases of trauma that leave the patient with a loss of functionality at the given site. These tissue transfers often include muscle transplantation in order to restore function at the defective location. For example, functional reconstruction may target trauma wounds of the face or a lower extremity.

Microvascular free tissue transfer makes use of vascular anastomosis, a surgical technique in which two blood vessels are connected via suturing of the two open ends. In free tissue transfer, the artery and vein of the transplanted flap is anastomosed to the vessels at the recipient site. Initially, the flap is perfused through the pedicle vessel until endothelialization is complete after the first two weeks. As a result, risk of flap compromise is greatest immediately after surgery when there is a sole means of perfusion for the newly transplanted tissue.

Complete flap failure, which refers to failure of the tissue on the microvascular level, is the most severe of these outcomes. At this stage, vascular anastomosis has essentially failed and the flap is no longer viable. Less common is partial flap necrosis, which generally occurs as a result of flap planning errors or an underlying hematoma exerting pressure on the flap.

The risk for flap failure is the greatest in the first 48 hours after surgery. There are a number of factors that may put a patient at greater risk of failure than others during this timeframe. These factors can further be separated into two categories: patient-related and surgery-related. The former includes both natural and behavioral factors that predispose the patient to vascular complications that can indirectly lead to failure. For example, patients with diabetes have a greater risk of peripheral-vascular disease, which calls for supplemental vascular evaluation post-surgery. Additionally, behavioral factors such as tobacco and alcohol use are associated with vascular spasms and acute alcohol withdrawals, respectively, which put the patient at increased risk of flap failure. Surgery-related factors are those associated with the flap transplant itself. One of the most critical factors in ensuring the success of the operation is the quality of vessels at the recipient site. The artery is preferably smooth with pulsatile red blood flow, and the vein should be compliant with centripetal blood flow. Another important surgical consideration is the ischemic toleration level of the flap. For example, skin flaps are relatively tolerant of ischemia, whereas muscle flaps are less tolerant and have a lower salvage rate in the instance of any complications. Finally, recipient sites with increased incidence of complications, such as lower limb sites and poorly vascularized sites, can put the patient at greater risk of flap failure.

Thrombosis remains the most common cause of flap failure, occurring in approximately 10-12% of all free tissue transfers. Venous occlusion is more prevalent than arterial, although arterial compromise can be significantly more problematic. The salvage rate for occluded flaps ranges from 28-90% and depends greatly on origin of thrombosis as well as the risk factors discussed previously. Technical errors are a common cause of occlusion, especially those associated with vascular anastomosis, flap design, and tissue elevation. Compressive forces on the vascular pedicle as a result of hematoma or tight closure can also lead to thrombosis.

Hematoma in the absence of thrombosis is the second most common cause of flap compromise, occurring in approximately 2-4% of all free flap surgeries. This occurs when blood pools outside of the vessels in the tissue itself, causing swelling and other complications. Hematoma-related flap failure that occurs in the absence of vascular pedicle occlusion is distinctly different than pressure-induced thrombosis. In this case, the mechanisms of flap necrosis are biochemical in nature rather than mechanical. There are a number of chemical and cellular processes that may be responsible for subsequent tissue ischemia, including the release of proteolytic enzymes and reactive oxygen species as a result of platelet degradation in the tissue.

In most cases of postoperative complications, flap salvage is possible with rapid detection and immediate re-exploration of the compromised tissue. Salvage rates for flap can vary significantly depending on the source of the complication. For example, a study of 2372 head and neck free tissue transfers found that thrombectomy after venous occlusion was successful 60% of the time, whereas arterial thrombectomy had a success rate of only about 15%. Additionally, the location of the tissue can significantly impact the salvage rate of the flap. Another study of 716 free tissue transfers reported a greater failure rate for buried flaps (7%) versus non-buried flaps (2%) due to inadequate postoperative monitoring of buried flaps.

It is critical that flap compromise is detected as early as possible for the best chance of salvaging the tissue. In general, the salvage rate is much lower for flaps that undergo late re-exploration. A study of microvascular free tissue transfer in 21 cases of head and neck reconstruction found that the average re-exploration time for non-salvaged flaps was 3.9 days, in comparison with 1.3 days for successfully salvaged flaps. Thus, careful monitoring and early detection of complications is vital for preventing flap failure.

After undergoing microvascular free tissue transfer, patients are frequently monitored in the ICU by in-house nursing staff. Patients are kept on strict bedrest for the first 24 hours to limit the risk of postoperative complications. To prevent vascular occlusion of the newly transplanted flap, additional precautions are taken to prevent anemia and keep the patient well hydrated. In cases of head and neck reconstruction, tracheostomy is a routine procedure used to provide a pathway for breathing. Careful attention must be paid to the positioning of the tracheostomy to ensure that it does not exert excessive pressure on the flap.

Clinical examinations are given every hour for the first 24 hours, followed by every two hours for the next 48 hours, and finally every four hours until discharge. During these examinations, the health of the newly transplanted tissue is evaluated using six parameters: color, turgor, capillary refill, prick test, temperature, and Doppler ultrasound.

Visual examination by a nurse is used to evaluate the flap's color. A healthy, well-perfused flap will appear pink in color. A bluish hue may indicate venous occlusion, whereas a pale flap may suggest arterial occlusion.

Turgor of the flap is assessed by pinching a portion of the tissue for a few seconds and releasing it to evaluate how quickly it returns to its original state. Healthy flaps will appear minimally edematous, meaning that there is little to no swelling in the tissue. An accumulation of fluid in the flap is one of the first visible signs of thrombosis, and may indicate occlusion of the primary vein.

Capillary refill is performed by applying pressure to the surface of the tissue with a fingertip and releasing the pressure to evaluate the reperfusion of the tissue. A healthy flap will exhibit a capillary refill time of approximately 2-3 seconds. Venous occlusion will result in a shortened capillary refill time (less than 2 seconds), whereas arterial occlusion will have an increased capillary refill time (greater than 3 seconds).

The prick test is conducted daily to evaluate dermal bleeding in the flap. Using a 25-30-gauge needle, the surface of the tissue is punctured and the resulting blood flow is observed. This may be performed at multiple points on the flap to ensure proper perfusion across the entire surface. A healthy flap will show immediate, bright red blood flow. Dark blood is potentially indicative of venous occlusion. A flap that exhibits delayed blood flow beyond twenty seconds or no flow at all may be experiencing arterial thrombosis.

Temperature is evaluated by palpation of the flap or temperature strip indicators placed on the surface of the tissue. Healthy, well-perfused tissue should feel warm to the touch. An acute decrease in surface temperature of 3° C. may indicate arterial occlusion, whereas a uniform drop of 1-2° C. suggests venous occlusion.

Finally, Doppler ultrasound is used to evaluate blood flow through the flap. One method for monitoring this parameter is using a handheld Doppler probe, which is placed against the surface of the tissue in order to obtain an acoustic Doppler signal. Immediately after surgery, the locations of the arterial and venous vessels are marked on the surface of the tissue to provide guides for postoperative monitoring measures such as Doppler ultrasound. Additionally, arterial flow can be distinguished from venous flow due to the pulsatile nature of the signal. Arterial occlusion can be detected by loss of the Doppler signal across the flap. However, it takes a highly trained ear to be able to detect the more subtle changes leading up to complete arterial occlusion or to be able to detect venous occlusion, as the arterial pulse may still be present in the signal.

Temperature of the newly transplanted flap is a simple and reliable method for determining the health of the tissue. As a transplanted flap acclimates to its new location at the recipient site, the tissue reaches normal body temperature of approximately 37° C. In the event of vascular occlusion, blood perfusion through the flap is compromised and a corresponding drop in temperature is exhibited in the flap.

Thermistor probes are a simple and cost effective method for measuring temperature in free tissue. A major advantage of them over the currently accepted temperature strip method is that they can be used to continuously measure temperature near the surface of the flap. A thermistor changes its resistance based on temperature so it can be used to transduce a temperature into a corresponding voltage. Their placement at the surface of the flap, however, does subject them to a lot of variation caused by differences in temperature of the room and other factors. This makes them an unlikely candidate for reliable monitoring of the flap but they noninvasive and easy to implement so therefore good to have in addition to measuring other parameters.

Thermal imaging is a much more sensitive way of measuring temperature. It is based upon the principle that heat emits energy in the infrared wavelength which can be picked up by an infrared camera. Pedicle flaps in rats enable one to thermally see the blood vessels supplying the flap as well as the subtle changes due to variations in flow caused by different angles of elevation. Major disadvantages to thermal imaging for the purposes of continuous monitoring are that it requires bulky and very expensive equipment, especially if each patient required their own separate unit.

Doppler ultrasound flowmetry operates on the principle of the Doppler shift: when a wave of some frequency is reflected by an object travelling at some velocity, the frequency of the reflected wave will be shifted with respect to the frequency of the incident wave by a factor directly proportional to the velocity of the struck object. This principle can be applied in the body to measure the velocity of blood by relying on particles in the blood such as red blood cells to reflect an ultrasonic wave at some shifted frequency. In one embodiment, an ultrasound probe can use two piezoelectric crystals to simultaneously emit and receive ultrasonic waves and the difference in frequency between the two can be audibly played to characterize the flow of blood in the region of interest. Ultrasound transducers can be placed on the flap at the surface, for noninvasive measurement, or they can be implanted directly around the blood vessel of interest, as in the case of the Cook-Swartz implantable probe.

External Doppler ultrasound probes are placed on the surface of the flap and directed towards either the vein or artery supplying the flap. They can be placed precisely in order to obtain a good signal. The signal can also be dependent upon the many layers of tissue between the probe and the blood vessel. Every interface between two different kinds of tissue is an opportunity for some of the ultrasound signal to reflect back to the transducer before making it to the blood vessel, hence the use of ultrasound gel to couple the transducer to the surface of the skin so that the entirety of the signal does not get reflected before even penetrating the epidermis. Additionally, different probe frequencies can be selected to adjust the penetrating depth where lower frequency probes will have a greater depth of penetration. The most common standard for monitoring is using a handheld Doppler ultrasound unit and audibly listening to the signal from the flap to diagnose its condition. This can prove unreliable due to the difficulty of recognizing subtleties in the signal. Some advantages of using Doppler ultrasound is that it is already readily available in many hospitals and is a noninvasive method of measurement. However some of the disadvantages are the need for attending physicians to continually check on the patient and manually perform the recording and also that the effectiveness is highly dependent on the particular physician's skill level in listening to flaps.

Implantable Doppler probes are an effective method for measuring Doppler ultrasound in newly transplanted flaps. Unlike the external Doppler probe, these probes are not as affected by the attenuation of the signal through layers of intermediary tissue as they are wrapped directly around the blood vessel of the flap during surgery and left in for postoperative monitoring. As such, the signal recorded is always from the probe in the same orientation because it does not need to be continually repositioned to search for the signal like probes on the surface of the flap. Implantable Doppler probes have been shown to detect signs of occlusion earlier than clinical methods. Some studies have previously shown that when placed on the artery, implantable probes are capable of immediately detecting arterial occlusion and venous occlusion after 220±40 minutes and when placed on the vein they are capable of immediately detecting venous occlusion and arterial occlusion after 6±2.4 minutes. However, implantable Doppler probes also have a number of disadvantages that limit their use for clinical monitoring. Recent studies have shown false positive rates of approximately 10% amongst flaps that have been monitored using implantable Doppler methods. More significantly, implantable probes have been shown to cause venous congestion in some cases due to excess pressure around vessel. So while the venous placement would seem necessary for accurate detection, it subjects the more delicate venous anastomosis to potential complications. This is a critical limitation of implantable Doppler technology, especially for use in free flap monitoring where vascular flow can be easily compromised. This can also interfer with the use of other sensors that can also contribute significant information for a reliable repeatable measurement.

Laser Doppler flowmetry operates on the Doppler shift principle, similar to Doppler ultrasound flowmetry, but it uses waves of light instead of sound. Light being a much higher frequency does not penetrate as deep as sound and laser Doppler flowmetry looks at blood perfusion approximately 1-2 mm under the surface instead of blood flowing through larger blood vessels as Doppler ultrasound might. It works on the principle that a single wavelength of light, a laser, can be emitted into the tissue and what is reflected will be a combination of light that has been Doppler shifted due to coming into contact with moving particles and light that has not. The amount of Doppler shifted light and the amplitude of that shift correlate to the perfusion of blood in the subcutaneous layers.

Laser Doppler flowmetry is highly effective for detecting both venous and arterial occlusion. A study of free flap monitoring in maxillofacial reconstruction found that laser Doppler flowmetry was able to detect signs of vascular occlusion earlier than traditional clinical assessment. However, there are a number of inherent limitations associated with this method. Namely, laser Doppler signal requires careful interpretation. Generally, arterial occlusion results in an abrupt decline of flow values, while venous occlusion results in a more gradual decline. However, in many cases it can be difficult to distinguish between the two using laser Doppler flowmetry. A healthy flap will have a pulsatile waveform and fluctuations in the waveform caused by normal vasomotor and physiological processes. A failing flap may show a lack of pulsatility or fluctuations. Because laser Doppler flowmetry does not measure in any physically relevant units, all measurements are relative and determinations about the flow in the flap need to be made in reference to baseline values.

Measuring pH has proven to be an effective method for detecting both venous and arterial occlusion in newly transplanted tissue. Prolonged vascular compromise initiates an ischemic cascade in tissue. Lack of oxygen in the tissue results in a failure of ATP production, causing cells to switch to anaerobic metabolism. This leads to buildup of lactic acid in the cells, causing a drop in pH across the tissue. This can be seen very clearly in Table 1 below. Thus, acidosis of the tissue is one of the first indicators of flap failure. By monitoring pH it is possible to determine whether there is a vascular insufficiency in the flap and also even the extent to which the flap has become ischemic and whether it is still viable or not. pH is likely the most promising of all the physiological parameters to measure for an accurate representation of the condition of the flap however none of the currently available sensors meet the requirements necessary for monitoring in microvascular free flap applications.

TABLE 1 pH drop in compromised flaps for five minute intervals after vascular compromise

| Time post occlusion (mins) | Artery only (6 flaps) | Artery and vein (4 flaps) | Vein only (4 flaps) |
| --- | --- | --- | --- |
| 0 | 7.43 | 7.44 | 7.43 |
| 5 | 7.34 | 7.35 | 7.41 |
| 10 | 7.27 | 7.28 | 7.38 |
| 15 | 7.18 | 7.23 | 7.35 |
| 20 | 7.12 | 7.16 | 7.33 |
| 30 | 7.06 | 7.10 | 7.29 |
| Overall drop in pH | 0.37 | 0.34 | 0.14 |

Ion sensitive field effect transistors (ISFET) are a solid-state device sensitive to pH. They are not very accurate and readings can vary as much as 0.34 pH units due to temperature alone. Drift over extended periods exceeds 1 pH unit. Other limitations of this technology are the brittleness of the silicone substrate, which limits applications of ISFET in-vivo. Additionally, encapsulation of the sensor has proven to be problematic due to the need to separate the inner wiring from the fluid being measured. In conclusion, they would not be suitable for integration in a continuous free flap-monitoring device.

Fiber optic pH sensors operate on the principle of measuring hydrogen ion activity or concentration. This is done optically using a pH sensitive dye, often phenol red for its sensitivity from pH 6.8 to 8.2, bound to a fiber optic cable. The dye absorbs different wavelengths of light depending on the pH and this is detectable by the fiber optic transducer.

Fiber optic pH sensors are advantageous for in-vivo use because they do not require an electrical current to be passed and thus are perceived as a safer method. Also the sensor tips can be made very small to be minimally invasive. A major disadvantage is that they are prone to drift and are not accurate over extended period of time and also surgeons can be uneasy about implanting glass into the flap for the potential of it breaking. They would not work for the application of continued postoperative flap monitoring because the five-day period of monitoring would render their results unreliable.

Glass microelectrodes have the necessary accuracy and precision to within 0.01 pH units for measuring pH in-vivo and have found to be more stable than the other methods by comparison. A major disadvantage to these electrodes is the necessity for calibration prior to use and multiple reference electrodes to minimize the drift over extended periods of time. This makes set-up cumbersome and time consuming, which is not something the surgeons would desire to do after a long and tedious surgical procedure. Further, delicate glass electrodes become a liability when implanted in the flap if they were to break.

Near infrared spectroscopy is a noninvasive method for measuring pH that correlates reflectance near infrared spectra to tissue pH. Every molecule reflects a specific and unique spectrum, which makes near infrared spectroscopy an invaluable tool in the identification of chemical species. Using it to measure oxygenation is also fairly straightforward. However, because of the multitude of factors that simultaneously contribute to the pH of tissue it is extremely difficult to correlate across the many confounding factors. There is no single way to claim that a given spectrum correlates to a certain pH. It would be necessary to perform multivariable calibration for each individual species or even subject type being measured because of confounding factors such as penetration depth, tissue color, variations between muscle and fat, and many more. Still, the method has shown some promise in a study utilizing five New Zealand White Rabbits where the pH of rabbits within the population could be determined from the calibrated spectra. It is not currently a feasible method for use in humans until much more data is collected, an endeavor beyond the scope of this project.

Oxygenation is measured by finding the percent oxygen saturation of hemoglobin in the blood. This protein is found in red blood cells and is responsible for transporting carbon dioxide and oxygen to and from the lungs, respectively. Oxygen saturation can be used as a means for evaluating arterial blood flow and tissue perfusion in newly transplanted flaps. Thrombosis results in a decrease of oxygenated blood both in the flap artery and throughout the tissue. This change can be detected using a number of different techniques and oxygenation parameters, including arterial blood gas ($SaO_2$), pulse oximetry ($SpO_2$), and NIR spectroscopy ($StO_2$).

$SaO_2$ is an invasive measure of arterial oxygen saturation that involves taking a sample of arterial blood and testing it with a blood gas analyzer. This measures the saturation of $O_2$ in the arteries, but is not a measure of tissue perfusion or oxygenation. A major disadvantage to this method is that it required invasive sampling of the blood and the analysis is often performed ex-vivo on large and expensive laboratory equipment.

$SpO_2$ is a noninvasive measure of arterial oxygen saturation that can be measured using a pulse oximeter. Pulse oximetry uses the principle of light absorbance to determine the oxygen saturation of hemoglobin. A study of pulse oximetry in vascular occlusion of a rabbit ear model found this method to be highly sensitive to arterial occlusion, producing an immediate response in the event of thrombosis. However, changes in $SpO_2$ were less pronounced in the event of venous complications, exhibiting only a gradual decline and consistent normoxemic levels after venous occlusion.

$StO_2$ is a measurement of tissue hemoglobin oxygen saturation that can provide indications of vascular compromise in newly transplanted tissue. Unlike $SaO_2$ and $SpO_2$, $StO_2$ measures the saturation of $O_2$ that has diffused into tissue cells. Thus, $StO_2$ can be used to evaluate tissue perfusion. Lack of oxygenated blood flow through the flap in the event of arterial or venous occlusion will result in a decrease in $StO_2$.

A device for noninvasively measuring $StO_2$ levels in free flaps using the principle of NIR spectroscopy. This device provides continuous, real-time $StO_2$ measurements and wirelessly transmits the data to any Wi-Fi enabled device.

The device of preferred embodiments described herein enables user interaction, sensor integration, intuitive user interface, and portability. The device can be used on patients in hospitals, clinics and provide self-monitoring at home or in outpatient settings.

It is critical that the probes used for monitoring are easy for the surgeon to implant within the tissue during the operative procedure. Sensor attachment must be taken into consideration, namely where in the tissue they will be placed. For example, a probe that requires precise placement around a blood vessel may be difficult to accomplish and compromise the usability of the device. Also, the bulkiness of the sensors needs to be taken into account as it affects the patient's overall comfort level during recovery.

The next secondary objective in this category is to develop an intuitive user interface for monitoring data. The tablet or smartphone application is easy for the surgeon to navigate. It is critical that the data is both accessible and easily interpretable. There is a notification system that alerts the surgeon at proper times with accurate and informative information.

Embodiments provide versatility, meaning that the device can be used for a wide range of flap monitoring applications. Namely, the device is adaptable to flaps of different sizes, tissue types, and locations. In order to achieve versatility, careful consideration must be given to sensor size, type, and attachment. Sensors must be chosen that are applicable to flaps of multiples sizes, different types (skin, muscle, etc.), and different locations (limb, abdomen, etc).

The device is upgradeable included in sensor interchangeability a wide range of flap transplants. Additionally, the device is designed such that new measurement techniques can be incorporated.

Taking this into consideration, it was determined that the device must be safe for the patient, compliant with existing protocols, and comfortable for the patient.

Monitoring of the flap must not threaten or disrupt the success of the transplantation. It is critical that the device does not pose a risk of vessel occlusion, hemorrhage, or any other physiological event that could disrupt blood flow or result in tissue death. Second, the biocompatibility of the device ensures the implantation of the sensors into the tissue or the attachment of noninvasive sensors does not elicit an inflammatory immune response at the site of contact. Material selection avoids rejection of the probes and ensures the safety of the patient. Finally, the device is designed in a way such that the probes can be adequately sterilized and implanted to avoid infection.

There are two primary procedures: intraoperative protocols and postoperative protocols.

Fixation of the probes to the tissue during the operation must not interfere with anastomosis, wound closure, or any other procedure of the transplant. It is vital that the device can easily be implemented into the current surgical protocols without compromising the success of the transplant. Similarly, the device must not complicate or interfere with the postoperative monitoring of the patient. Attachment of the device should not obstruct an attending physician's ability to assess the color, temperature, turgor, capillary refill, and Doppler ultrasound of the flap.

Fixation of the sensors to the tissue is achieved in such a way that it is virtually undetectable by the patient. Connection of the sensors to the main unit must also be taken into consideration to ensure that that the patient's movement is not excessively restricted due to wires or other features.

A number of ISO standards in place that must be considered including that the medical device must be sterile for using microbiological methods. Because the monitoring device is both invasive and multi-use, sterilization is critical for ensuring patient safety. Such a device must be free of all bacteria and other microorganisms to avoid the transmission of disease and infection and must have the biocompatibility for medical devices.

Algorithms developed in MATLAB for analyzing Doppler signals comply with industry standards. Similarly, all programming for the mobile interface meet the W3C standards for application development. The system preferably incorporates continuous Doppler and temperature, wherein the system collects, processes, and transmits the data. Additionally, the device uses variations in light absorbance in the tissue of the flap under differing vascular conditions and includes a light reflectance transducer to quantitatively and objectively evaluate the color of the flap to a degree of sensitivity unachievable by the human eye. The monitoring device provides ischemic detection in microvascular free tissue transfer by continuously collecting information from temperature, Doppler ultrasound, and light reflectance and processes this information to alert clinical staff to signs of complications as well as transmits this information wirelessly so that it can be accessed by the surgeons through a tablet or smart-phone application or web portal.

An exemplary schematic for a system 10 for measuring vascular deficiency is shown in FIG. 1A. The system 10 can include a control unit 12 connected to a Doppler ultrasound probe 20, a temperature probe 22, and/or a color probe 24. The control unit 12 can include a controller 16, a user interface 18, and a networked processing system 14. The system 10 can acquire temperature and Doppler ultrasound data one or more of the probes. In some embodiments, the control unit 12 can apply algorithms to process the data in order to detect variance indicative of vessel occlusion and can transmits the information wirelessly to store the information remotely. In some embodiments, the control unit 12 can display the data on an graphical user interface (GUI) and/or alert clinicians of a possible occlusion.

Figure 1B:
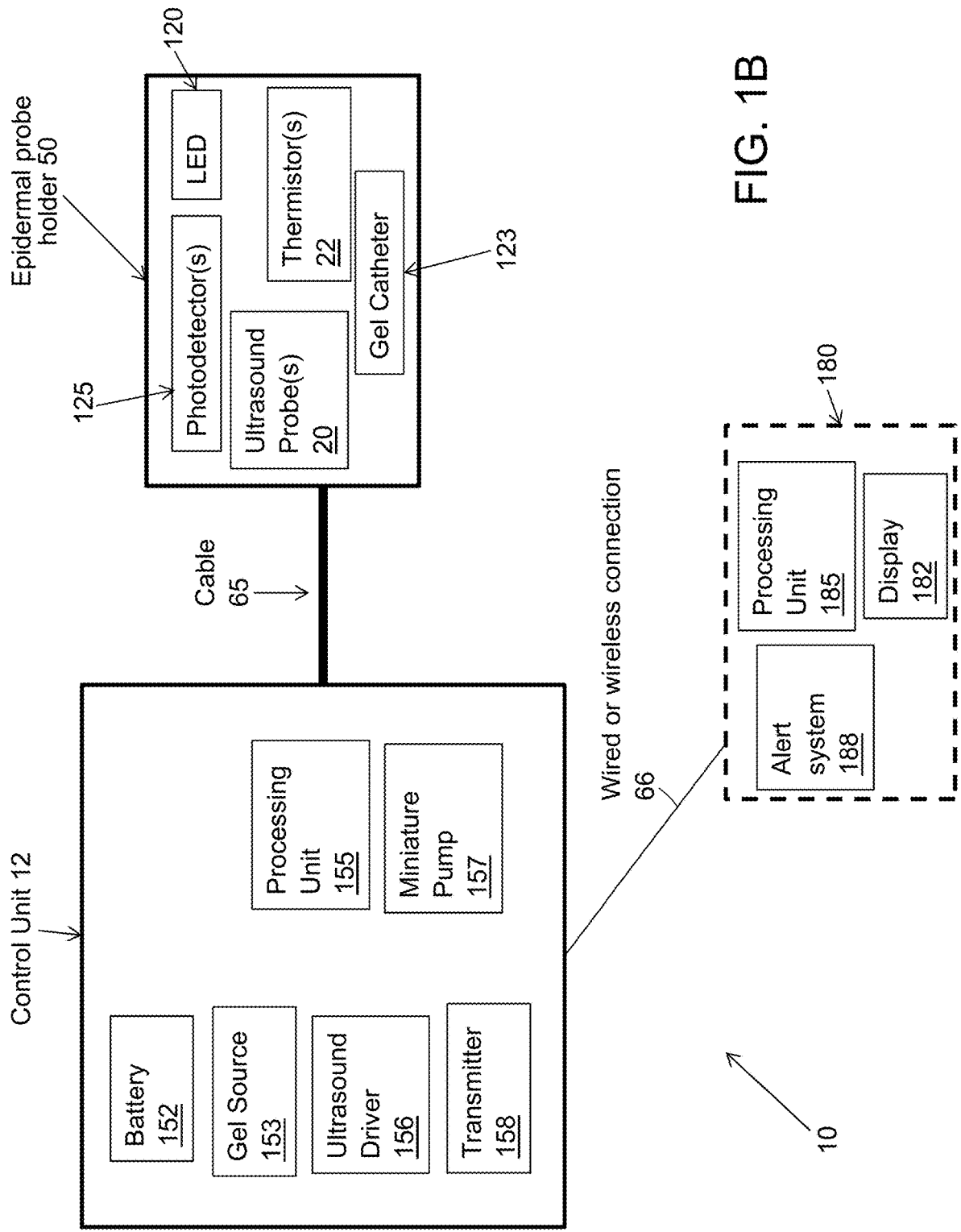
FIG. 1B illustrates a block diagram for a system for measuring vascular deficiency in accordance with various embodiments described herein.
Figure 1D:
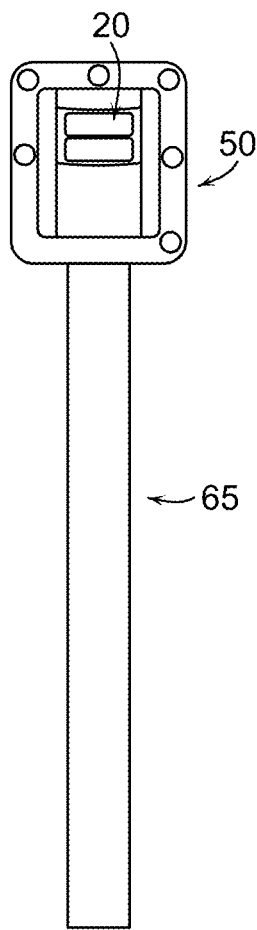
FIG. 1D shows a probe for a system for measuring vascular deficiency in accordance with various embodiments described herein.

In some embodiments, the system 10 can include a control unit 12, an epidermal probe holder 50, and a display unit 180 as shown in FIGS. 1B, 1C, and 1D. The epidermal probe holder 50 and control unit 12 are connected by one or more cables 65. The epidermal probe holder 50 can include one or more Doppler ultrasound probes 20, one or more temperature probes such as thermistors 22, and a light source 120 and one or more photodetectors 125 that combine to form a color probe 24. The control unit can include a battery 152, gel source 153, ultrasound driver 154, transmitter 158, miniature pump 157, and a processing unit 155. Signals generated by the various probes of the epidermal probe holder 50 are sent to the control unit 12 via the cable 65. In various embodiments, the control unit 12 can process the signals using the processing unit 155 or the control unit 12 can send the signal data to the display unit 180 to be processed by a processing unit 185.

In some embodiments, the epidermal probe holder 50 can include a fluid or gel catheter 123 connected to a gel source 153 in the control unit 12 through the cable 65. The miniature pump 157 of the control unit 12 can push ultrasound conductive gel from the gel source 153 through the cable 65 to the gel catheter 123. The gel catheter 123 can emit the gel into a region between the surgical site and the Doppler ultrasound probe(s) 22 to create the necessary ultrasound connection between the probe and the tissue. The miniature pump 157 of the control unit 12 can continuously or discretely replenish the conductive gel through the gel catheter 123 to replace gel that has evaporated or been absorbed into the tissue.

In some embodiments, a user can interact with the display unit 180 to view or access information related to the processed signals received by the control unit 12 from the probes of the epidermal probe holder 50. For example, information about the current status of the tissue can be shown to the user on the display 182. In some embodiments, the display 182 may show a graphical user interface that can be manipulated by the user through a touchscreen or other controls 184 on the display unit 180. The display unit 180 can be connected to the control unit 12 using a wired or wireless connection 66.

In accordance with various embodiments, the epidermal probe holder 50 can be affixed at a surgical site to detect one or more physiological characteristics of a tissue transplant. For example, the epidermal probe holder 50 can be affixed at the surgical site using sutures or adhesive or can be bound at the surgical site by or as part of a dressing.

The control unit 12 can receive detected physiological data produced from the one or more probes using an interface to monitoring logic that is responsive to the probe. In some embodiments, the monitoring logic can be the processing unit 157. In some embodiments, the control unit 12 can be pocket-sized or wearable so as to improve portability of the system 10 for the patient. In some embodiments, the control unit 12 can be clipped to a belt. In some embodiments, the control unit 12 can be a body-worn processor housing.

The control unit 12 or display unit 180 can analyze the signals and physiological data received from the probes in the epidermal probe holder 50. In some embodiments, the analysis occurs automatedly and iteratively. The results of the analysis can include the condition of tissue at the surgical site that is indicative of reduced vascular flow in the tissue transplant. This tissue condition can be displayed on a display 18, 182 using a graphical user interface.

The first functional aspect of the device is collecting periodic data from temperature sensors 22 (such as thermistors) and Doppler ultrasound probes 20. This involves the following components: (1) temperature data acquisition, (2) Doppler ultrasound data acquisition, and (3) and optionally imaging data acquisition.

The system collects consistent temperature recordings over the monitoring period. Preferably the device detects a temperature differential of 2° C. or more. The temperature measurements are accurate to within 0.1° C. in order to ensure that variations in temperature are reported accurately. Additionally, the monitoring method is preferably inexpensive and sensitive to changes in temperature at the surface of the skin.

The device can use thermistors to measure the temperature at the different probe locations. Configured in a simple voltage divider, it was possible to get temperature measurements resolved to 0.1° C. with 10K thermistors and the 10-bit analog to digital converter built in to the controller (Arduino) that the device uses for data acquisition. Note that 100 k thermistors can be used for higher sensitivity in the range of desired temperatures with 1% tolerances for the consistency across different probes.

Doppler ultrasound data acquisition enables collection of signals from at least one and preferably at least two locations on the flap so that an arterial and a venous signal can be captured. Also, the device must be capable of switching between audibly playing the real time Doppler signal for probe placement and silently capturing the Doppler signal for remote monitoring.

Figure 2:
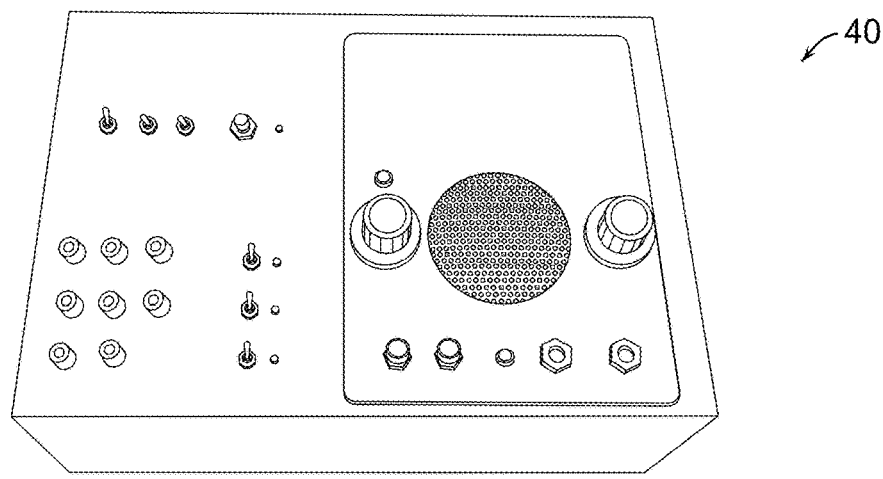
FIG. 2 illustrates a console and user interface for operating at least a portion of the system.

FIG. 2 depicts an embodiment of a device case 40 for the control unit 12 with all of the components integrated into the control panel. The switches and buttons that control general device function can be seen on the left side of the panel, and the Doppler flow meter control component can be seen on the right.

A preferred embodiment of the device can use of a Parks Medical model 811-B Doppler ultrasound box and interface with the probe input channels and headphone output port to record signals from multiple Parks Medical infant flat Doppler probes. Probe signal wires plug into a multiplexing circuit controlled by the device which selects which probe signal is fed to the Doppler box. The device then records the corresponding Doppler device output from the headphone output port. Using this method, the device can collect signals from at least two Doppler probes and optionally can use more probes. In order to be able to switch between silently and automatically to capture the Doppler signals for remote monitoring and playing the signal out load on demand in real time, a Panasonic TQ2-5V Low Signal Relay is used to switch the signal between the headphone output or microphone output of the Doppler box.

Figure 3A:
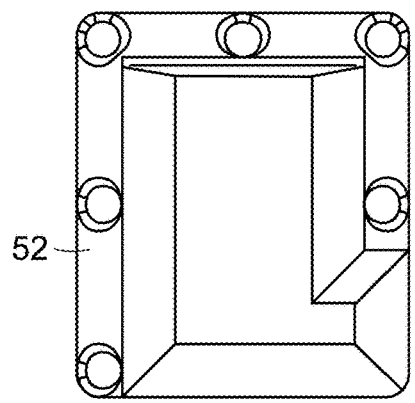
FIGS. 3A and 3B illustrate views of a housing for an ultrasound probe with a temperature measuring element include a gel catheter in accordance with systems described herein.
Figure 3B:
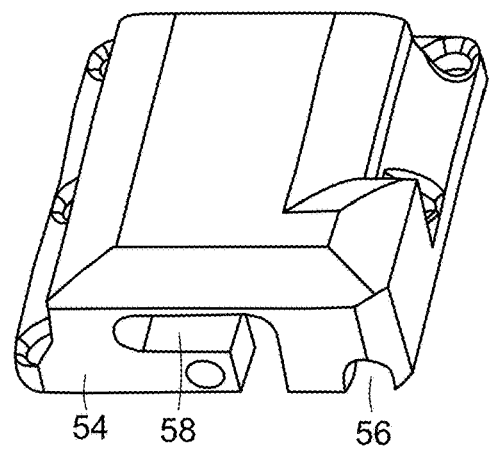
Figure 3C:
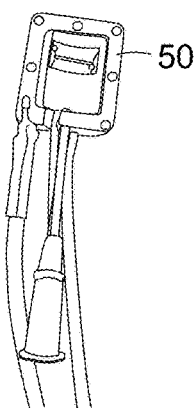
FIG. 3C shows an image of an assembled housing according to FIGS. 3A and 3B in accordance with various embodiments described herein.

An epidermal probe holder 50 in accordance with embodiments described herein is shown in FIGS. 3A-3C. The probe holder 50 provides consistent and effective data acquisition. The holder effectively holds a flat Doppler ultrasound probe, and/or a single thermistor. In addition to housing the probes, the holder is small and lightweight so as to not create excessive stress on the newly transplanted flap. The holder is securable to the skin for long-term monitoring (24-72 hours). Finally, the probe holder incorporates a method for preserving or replenishing ultrasound gel over the course of its use.

The probes or probe holder 50 can include adhesive patches to attach to the tissue transplant, e.g., the flap. These patches can be designed in several different sizes to adhere the Doppler probe 20 to the skin or the thermistor 22. In other embodiments, the patch can be of a size to attach the entire probe holder 50 to the skin. Several patches can be placed across the flap in appropriate positions. A hypoallergenic material such as cotton, coated in a biocompatible adhesive, can be used for the small probe holders. The adhesive portion is placed on the skin, fixing the probe against the skin.

The rectangular suturable probe holder 50 can be compact to house a single flat Doppler probe 20 and a thermistor probe 22 for temperature measurement. In addition to housing the probes, the holder can have a small port 58 for a 17-gauge gel catheter or tube 123 to be inserted to allow for the replenishment of ultrasound gel between the skin surface and the ultrasound probe. The gel is necessary to couple the probe to the tissue and it can dry out or be absorbed by the skin over time.

The device minimizes the size and weight of the holder, while maintaining the ability to secure the probes for an extended period of time. The gel delivery system enables the user to easily replenish the ultrasound gel beneath the Doppler probe, which is needed for long-term use of the probe holder 50.

In addition to collecting data and transmitting it, the device will continuously be performing analysis on collected data to detect problems with flap perfusion. Using information from both the temperature probes and Doppler probes, the device detects problems before traditional clinical signs become readily apparent.

A surface temperature differential greater than 2° C. between the surface of the flap and that of proximal tissue can be indicative of occlusion in the vascular supply to the flap. Therefore, in addition to plotting the temperature values for all of the probes, the device also computes the difference in temperature between the probes on the flap and off the flap. When this difference becomes greater than 2° C. it sends an alert to the clinicians cellular phone via text message and also displays an alert for that patient in the alerts section of the web interface. To assess the difference, the device uses the mean temperature from all of the probes on the flap in the last five minutes and compares it to the mean temperature from all of the probes proximal to the flap in the last five minutes.

Figure 4A:
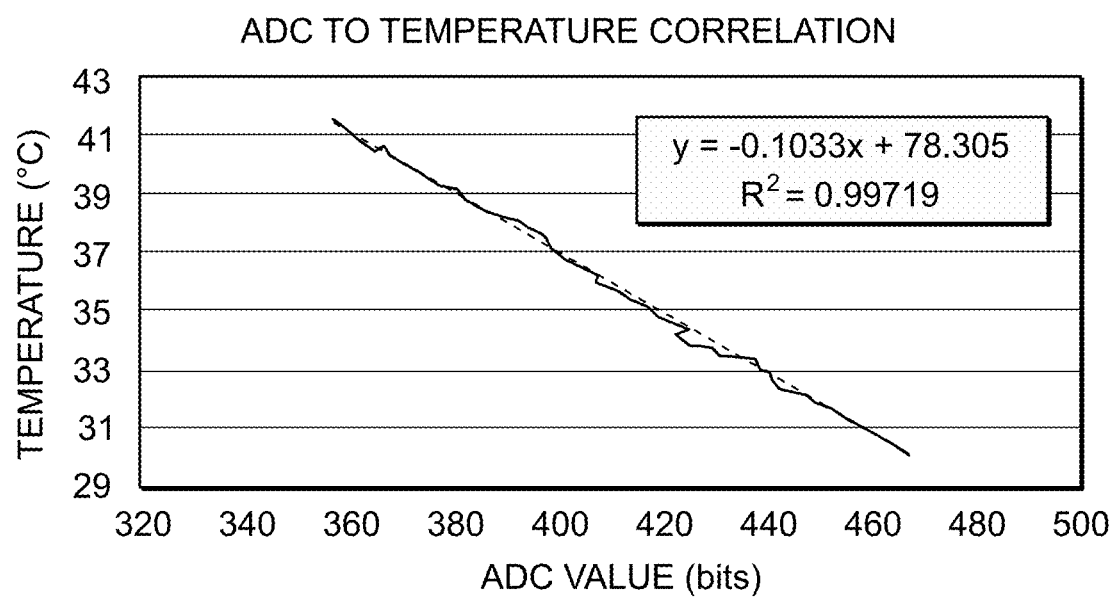
FIGS. 4A and 4B illustrate plots of temperature for measured thermistor values.
Figure 4B:
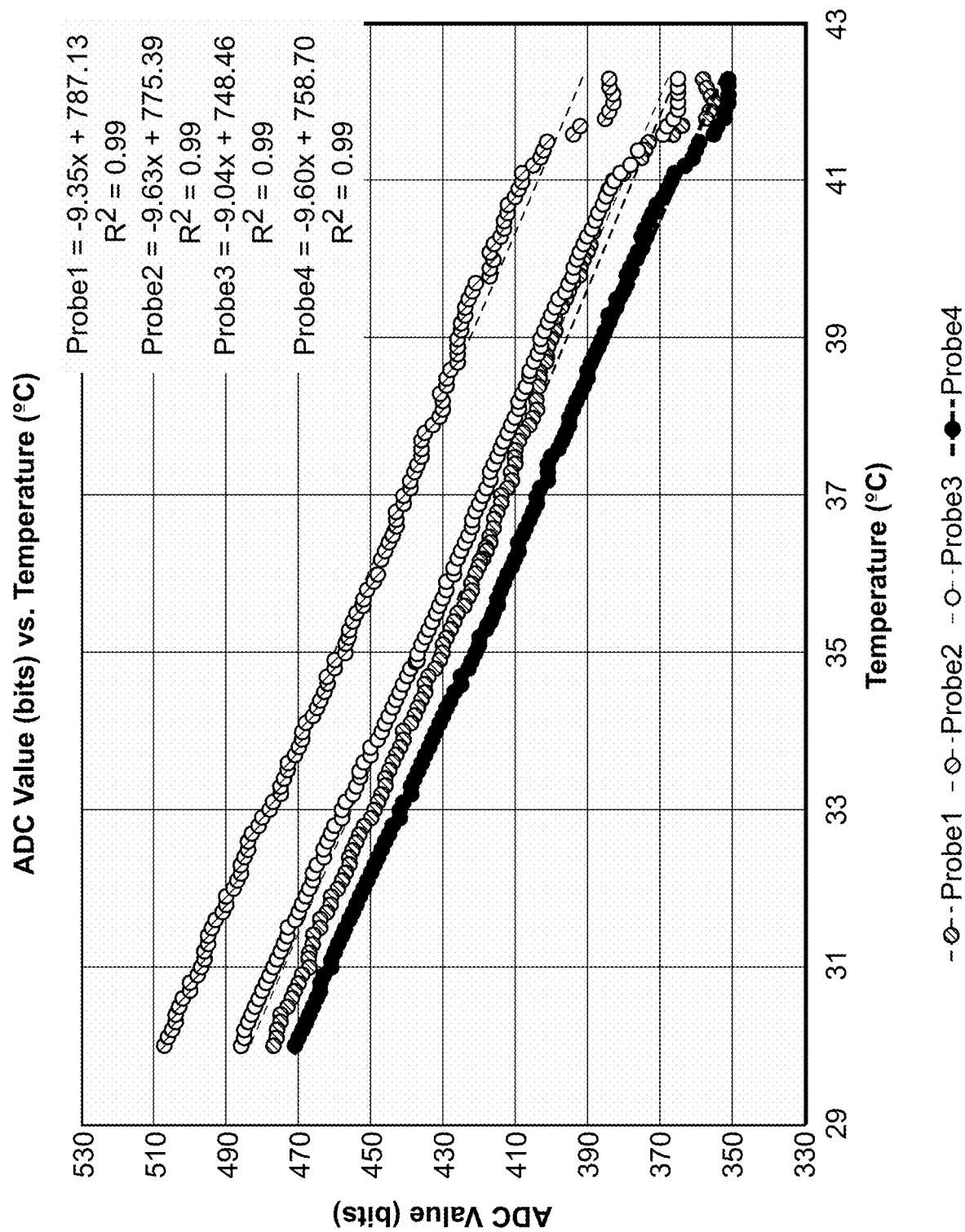

Thermistor calibration can be completed by measuring the resistance of the thermistors while submerged in a water bath at various temperatures. The thermistor 22 was wrapped in plastic wrap and placed in a water bath alongside a digital thermometer. Both were positioned such that they were fully submerged in the water and not in contact with the sides or bottom surface of the water bath. The plug end of the thermistor was connected to a digital ohmmeter and resistance values were obtained for temperature values for every 0.1° C. ranging from 31° C. to 38.5° C. The values were plotted and an equation was obtained for the calibration curve (see FIGS. 4A and 4B).

Figure 5:
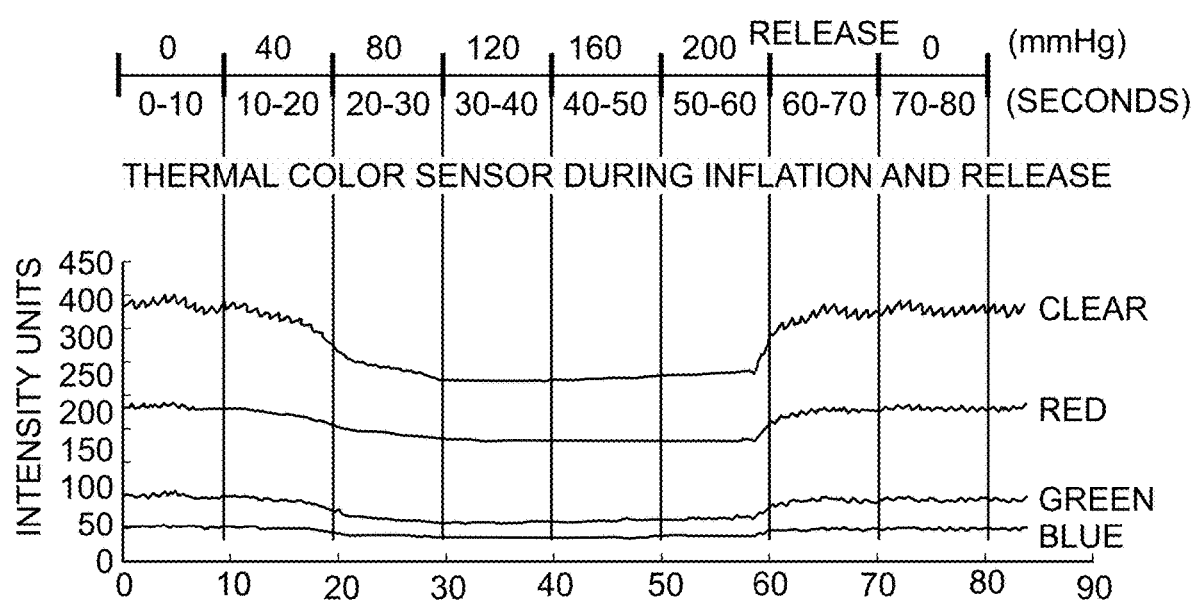
FIG. 5 illustrates a plot of color sensor results over time as pressure is applied and released.

An identical procedure to that used for temperature was used to evaluate the effectiveness of the color probe 24 at detecting sensitive changes in the tissue reflectance of red, blue, and green wavelengths with varying levels of perfusion. One transducer was placed on the forearm of each arm of the subject and continuous data was collected for the duration of the cuff inflation and subsequent deflation. FIG. 5 illustrates the four raw channels recorded from the color probe 24 Indicating the reflected amounts of white, red, green and blue light. The color probe 24 was able to detect sensitive pulsatile changes in blood volume corresponding to each heartbeat. Furthermore, the color probe 24 was capable of detecting changes in red and green absorption when the flow was occluded that would not be visible to the naked eye. The color probe can comprise one or more photodetectors or can be an imaging device such as a CCD or CMOS imaging device having at least 100,000 pixel elements.

Color of the flap is assessed using the TCS34725 RGB color sensor and a white LED. The two components are packaged together along with signal amplification and digital to analog converters in a small PCB board component available from Adafruit. The controller communicates with this unit over the I2C connection and is able to take readings of the amounts of red, green, blue, and clear light being received by the sensor after being emitted from the LED and reflected by the tissue.

The algorithm for the processing of Doppler ultrasound uses metrics such as the average power in a low frequency band indicative of venous flow, the area under the power curve for arterial occlusion, the presence of biphasic or triphasic components, or using a least mean squares approach to compare measured signals to reference signals indicative of different levels of occlusion. This provides robust detecting of arterial or venous occlusion from arterial, venous, or mixed signals across the range of sample signals.

FIGS. 6-11 depict the results of a controlled Doppler ultrasound study. The raw data was subjected to novel signal processing methods that allow for detection of and differentiation between venous and arterial occlusion. The power signals were plotted for each of the pressures (from 0 mmHg to 200 mmHg and subsequent deflation).

Prior to inflation (FIG. 6), the signal is unobstructed with a high baseline indicative of steady venous flow and healthy arterial pulses. At 40 mmHg (FIG. 7), venous flow has become occluded, which corresponds to the significant drop in the baseline signal. Arterial pulses are still present with biphasic peaks (the first peak is followed by a second, smaller peak), which indicates healthy arterial signal.

At 80 mmHg (FIG. 8), arterial flow starts to become compromised as the cuff reaches systolic blood pressure. The monophasic peaks (single peak with little/no secondary peak) are indicative of weak arterial signal. At 120 mmHg (FIG. 9), blood flow to the arm is entirely occluded and the signal disappears entirely. This persists for all pressures above 120 mmHg, where the cuff is above systolic blood pressure.

Upon releasing the pressure in the cuff, there is a return of arterial pulse (FIG. 10) and a subsequent return of venous flow (FIG. 11).

Figure 12A:
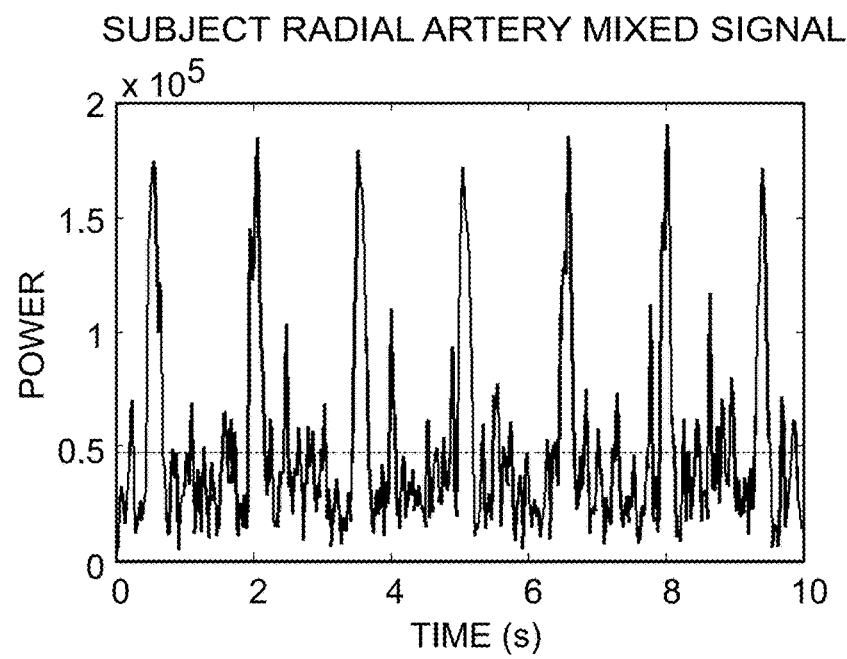
FIGS. 12A and 12B illustrate radial power signals over time derived from ultrasound measurements for a healthy subject and a postoperative subject.
Figure 12B:
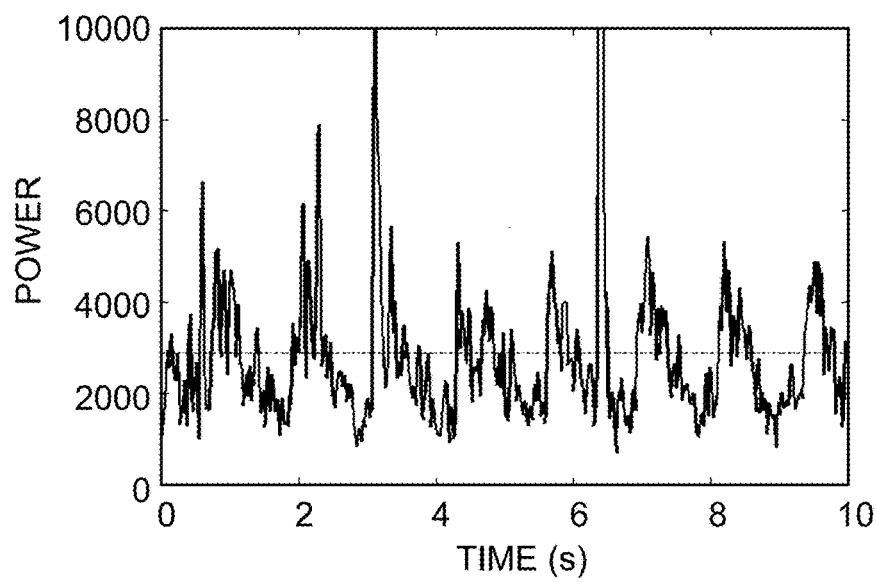

After successfully completing Doppler ultrasound trials on healthy volunteer subjects, the device was tested on a patient who had undergone a bilateral breast reconstruction. A flap Doppler ultrasound probe was placed over the breast flap, and a mixed arterial-venous signal was obtained. When compared to the signal from a healthy volunteer (FIG. 12A), the signal collected from the postoperative patient had the same characteristic shape, including the high baseline corresponding to venous flow and the biphasic peaks corresponding to arterial pulse (FIG. 12B). The ability of the system to obtain similar, high quality Doppler signal from flaps of different sizes and locations indicates that the detection algorithms can be applied to numerous types of flaps.

Figure 12C:
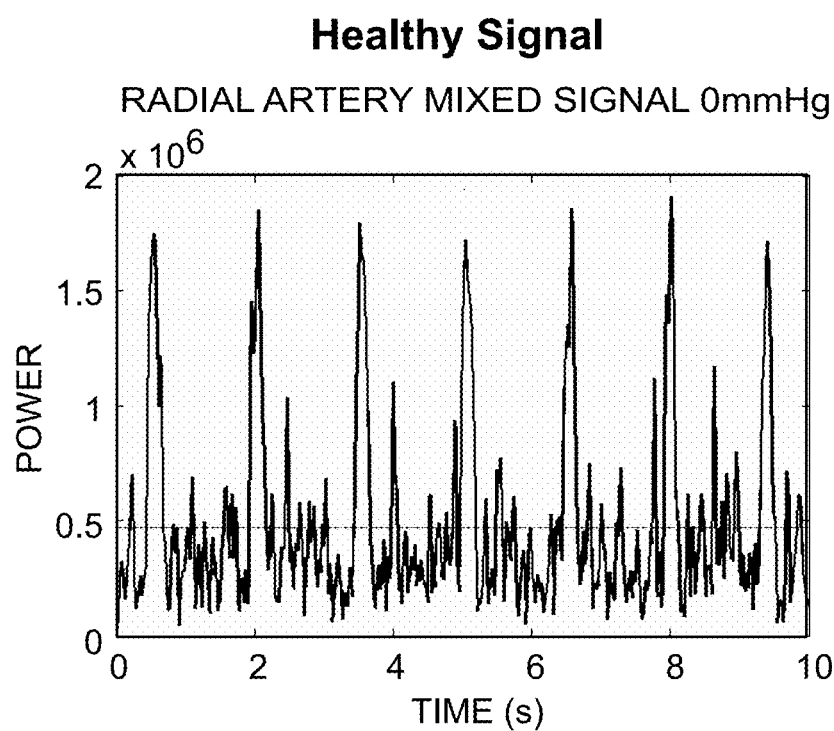
FIGS. 12C-12E illustrate radial power signals over time derived from ultrasound measurements representative of healthy perfusion, loss of venous signal, and weak arterial signal, respectively.
Figure 12D:
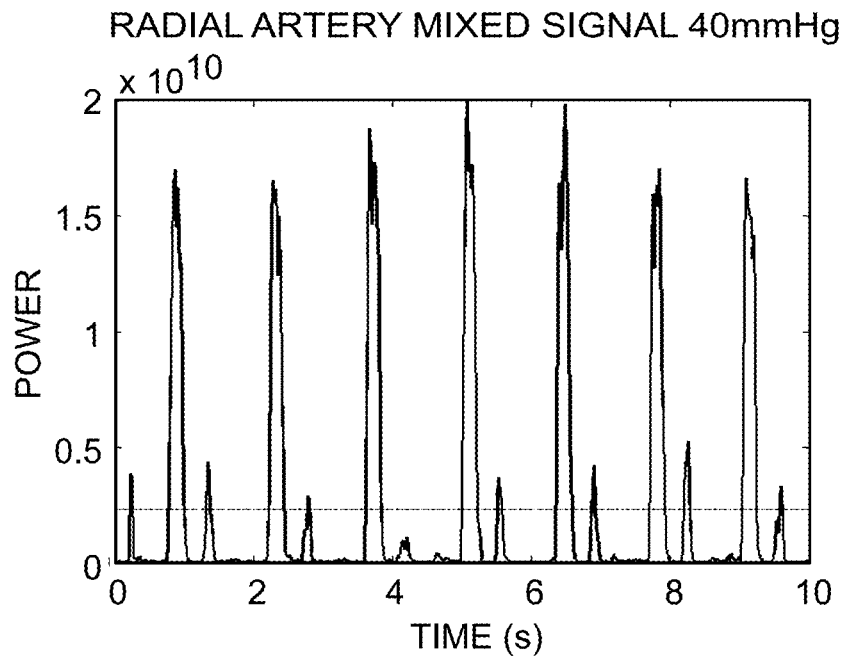
Figure 12E:
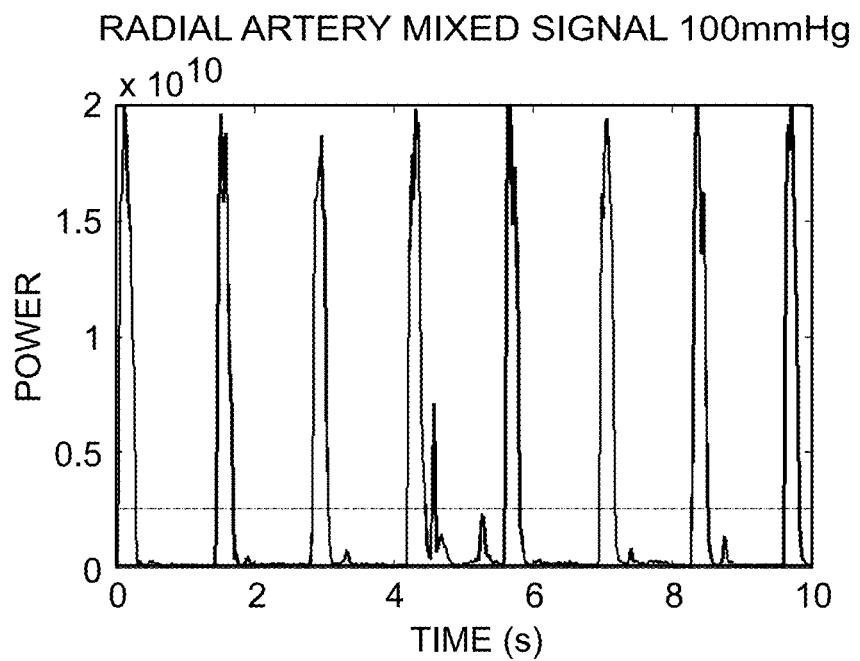

FIG. 12C again shows the signal for a healthy volunteer as shown above in FIG. 12A. By comparison, FIGS. 12D and 12E show threshold cases illustrating expected curves representative of loss of venous signal and weak arterial signal, respectively.

The remote monitoring aspect of the device primarily involved two components: (1) wireless transmission of the acquired data and (2) organization of the information in a database.

The device can connect to the Internet over a WPA2 secured wireless local area network in the hospital. There are two methods the device uses to communicate information with the remote server. The HTTP protocol's built in POST request method is used for simple transactions such as user interface events, temperature values, and Doppler recording filenames. The secure copy protocol (SCP) is used to transfer actual Doppler recording data files in uncompressed audio (.wav) format from the device to a directory on the remote server.

The database holds the information necessary to associate the device with a particular patient, remotely update the monitoring status of the device, relay temperature and Doppler data to the graphic interface, and secure the graphic interface in order to protect patient information. Also, in the database structure any patient identifying information (name) must be kept separate from relevant medical information (temperature and Doppler recordings).

The first database can comprise of seven tables, identified by the following titles: patients, deviceRequest, deviceStatus, alerts, doppler, temperature, and members. The contents and purpose of each table will be discussed in this section. For the binary attributes in each of the following tables, a value of 0 indicates the negative and a value of 1 indicates the affirmative.

The patients table comprises three attributes: patientID (a unique identifier for each patient in the table), lastname (the last name of the patient), and firstname (the first name of the patient). This table is used to store patient information for each individual registered with the monitoring system.

The deviceRequest table comprises five attributes: deviceID (a unique identifier for each device), patientID (the patientID corresponding to the patient who is assigned to the device with the given deviceID), temperature (a binary indicator of whether there is a request to turn on continuous temperature monitoring; 0 indicates no request, 1 indicates a request), doppler (a binary indicator of whether there is a request to turn on continuous Doppler monitoring; 0 indicates no request, 1 indicates a request), and dopplernow (a binary indicator of whether there is a request to turn on immediate Doppler monitoring; 0 indicates no request, 1 indicates a request). This table is used to pass information to the device regarding pending changes in monitoring status.

The deviceStatus table comprises five attributes identical to those found in the deviceRequest table. This table is updated once a request is passed to the device and the device monitoring status is updated accordingly. The reason for two identical tables is so a feedback loop can be created between the user interface controls and the device itself. When the device detects a request in the deviceRequest table, it completes the loop by changing its status and pushing that to the deviceStatus table. The user interface pulls status information from the deviceStatus table so if a request is made but for whatever reason does not reach the device, this would be reflected by no change in the devices status.

The alerts table comprises five attributes: alertID (a unique identifier for each alert), patientID (the patientID of the patient that the alert pertains to), epoch (the timestamp for when the given alert was issued), priority (the level of importance of the alert, from 0 to 2, 0 being the least important), and message (a string containing the message associated with the given alert). This table is used to store alerts that are displayed on the user interface.

The Doppler table comprises four attributes: patientID (the patientID of the patient that the recording belongs to), epoch (the timestamp for the given Doppler recording), probe (the number of the probe from which the Doppler recording was obtained), and filename (the name of the file under which the recording is saved in the directory). This table is used to store and organize the periodic Doppler recordings that are collected.

The temperature table comprises four attributes: patientID (the patientID of the patient that the recordings belong to), epoch (the timestamp for the given temperature recording), probe (the number of the probe from which the temperature recording was obtained), and value (the temperature value at the given instant). This table is used to store and organize periodic temperature recordings that are collected.

Finally, the members table comprises seven attributes: memberID (the unique member identifier), username (the username the member uses to login with), password (the password the member uses to login with, stored in encrypted form with SHA-512), email (the e-mail address associated with the member for activating accounts and resetting forgotten passwords), active (whether the member has activated their account), resetToken (a password reset token), and resetComplete (whether the password has been reset). This table keeps track of the authorized members who have access to the site. Members need to log-in through the welcome page in order to gain access to any of the device control or patient monitoring pages of the site. Their credentials are checked against those in the members table and if they match an active session is opened and each subsequent page checks whether the user if authorized before displaying any contents.

It is necessary for the end user to be able to control the device to start and stop the collection of data and also specify certain parameters about the probes installed and the patient they are currently on. Also, once the data is acquired and processed, it is must be displayed in such a way that it is easily accessible and interpretable by the clinician. Namely, this includes visual and audio representation of temperature and Doppler ultrasound recordings.

The graphical user interface is secure and protects all patient information which it contains. The physical user interface is simple to use and provide immediate access to any functionality that a clinician at the patient's bedside wants to activate such as switching the Doppler signal between silent recording and audible playback on the speaker.

Some embodiments for a graphical user interface were an iPhone application, a built in touch screen display on the device, and a web based user interface. A web based graphical user interface was decided upon as a good compromise because it can make the data acquired available remotely, it is easily customizable, and also it is portable and able to be viewed not only from a computer but also from the web browser of any smartphone. The system ports a "web application" to a native smartphone application using available online services. To complement the web user interface, which may have some minor delay in transmitting and receiving data and commands, the device includes a series of switches and status LEDs for immediate control at the bedside.

The graphical user interface was coded in HTML5, along with a CSS stylesheet for managing all of the stylistic aspects of the layout. All web pages of the GUI are initially redirected to a login page, where the user is prompted to enter their credentials: a username and password chosen by the user at the time of registration.

Upon entering their credentials and logging in, the user is redirected to their dashboard (FIG. 13), a platform for monitoring and managing the patients and devices associated with the user's account. The patients section contains a table summarizing each patient's temperature and Doppler monitoring status, as well as a list of each patient currently in the database.

Upon selecting a patient from the list, the user is redirected to the monitoring page associated with the particular patient (FIG. 14). This page contains the following sections: patient alerts (with prioritized messages pertaining to the patient's temperature and Doppler data), temperature data (a graph with real-time curves for each probe), and Doppler data (a list of timestamped Doppler recording files with a built-in player to listen to the recordings).

Figure 15:
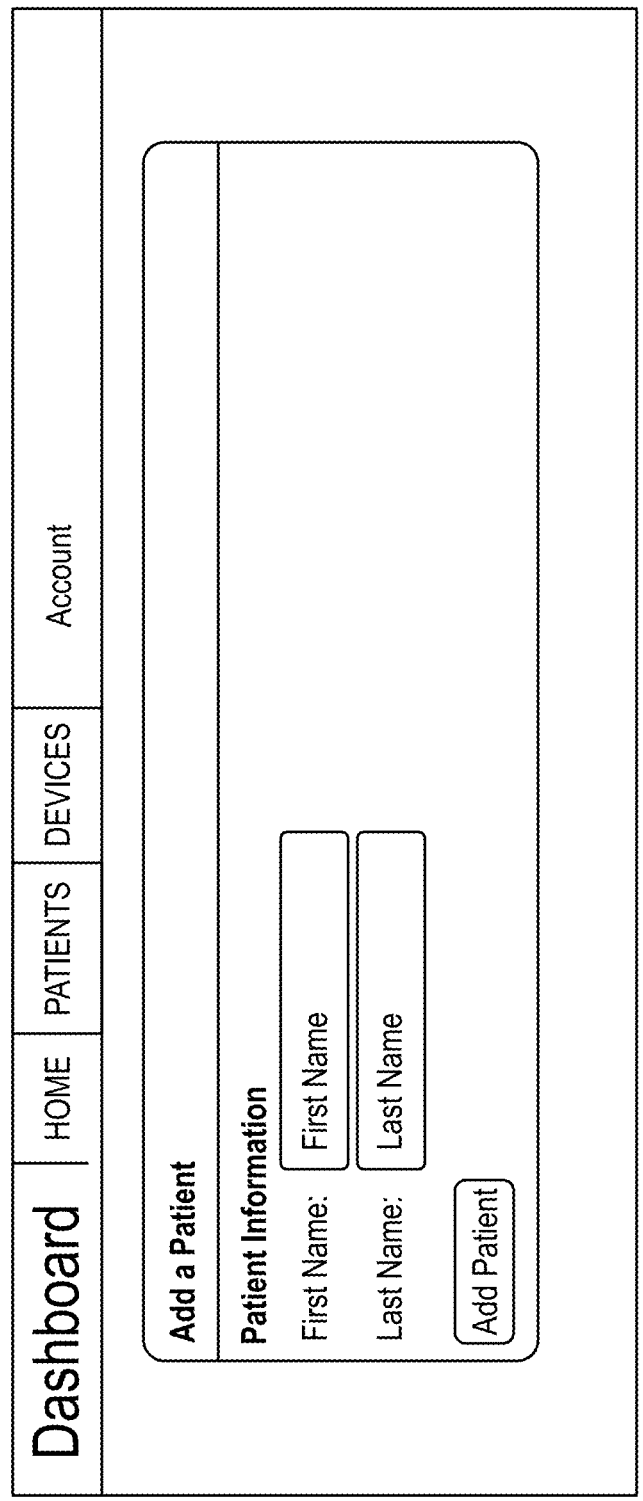
FIG. 15 illustrates an example graphical user interface for an add patient form in accordance with embodiments described herein.

An option is also included directly in the "Patients" navigation list for adding a patient to the database (FIG. 15). This redirects the user to a form that prompts them for the first and last name of the patient. Upon completing the form, a patient with the given information is automatically added to the database and a new page is generated for them displaying their data.

Figure 16:
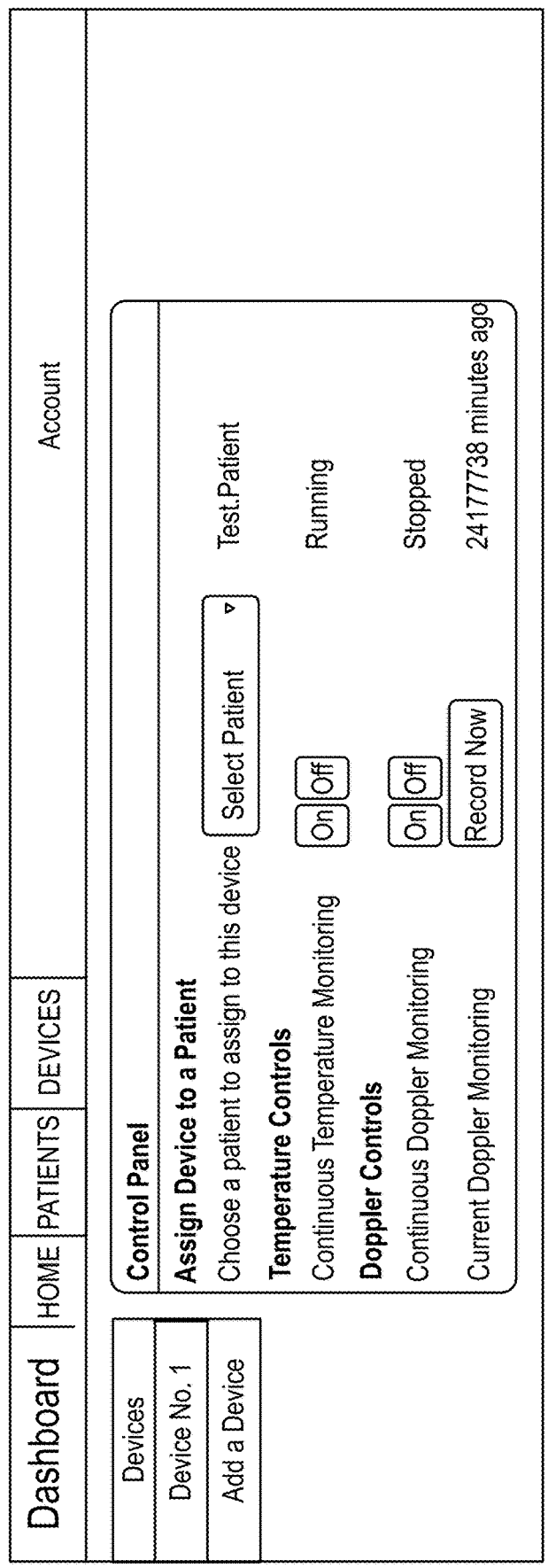
FIG. 16 illustrates an example graphical user interface for a device control panel in accordance with embodiments described herein.
Figure 17:
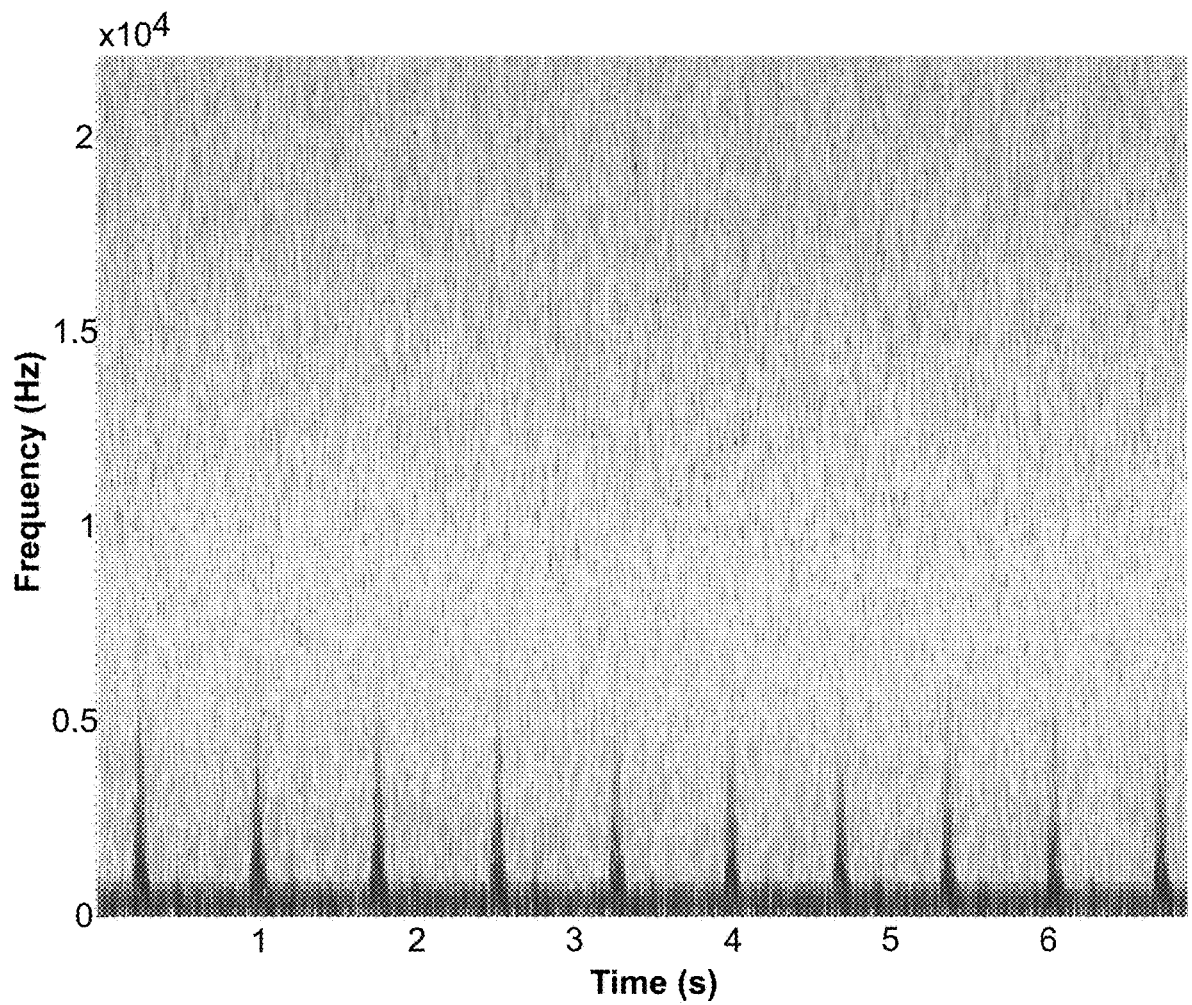
FIGS. 17-24 illustrate radial artery spectrograms derived from ultrasound data collected at increasing levels of applied pressure between 0-140 mmHg by the system in accordance with embodiments described herein.
Figure 18:
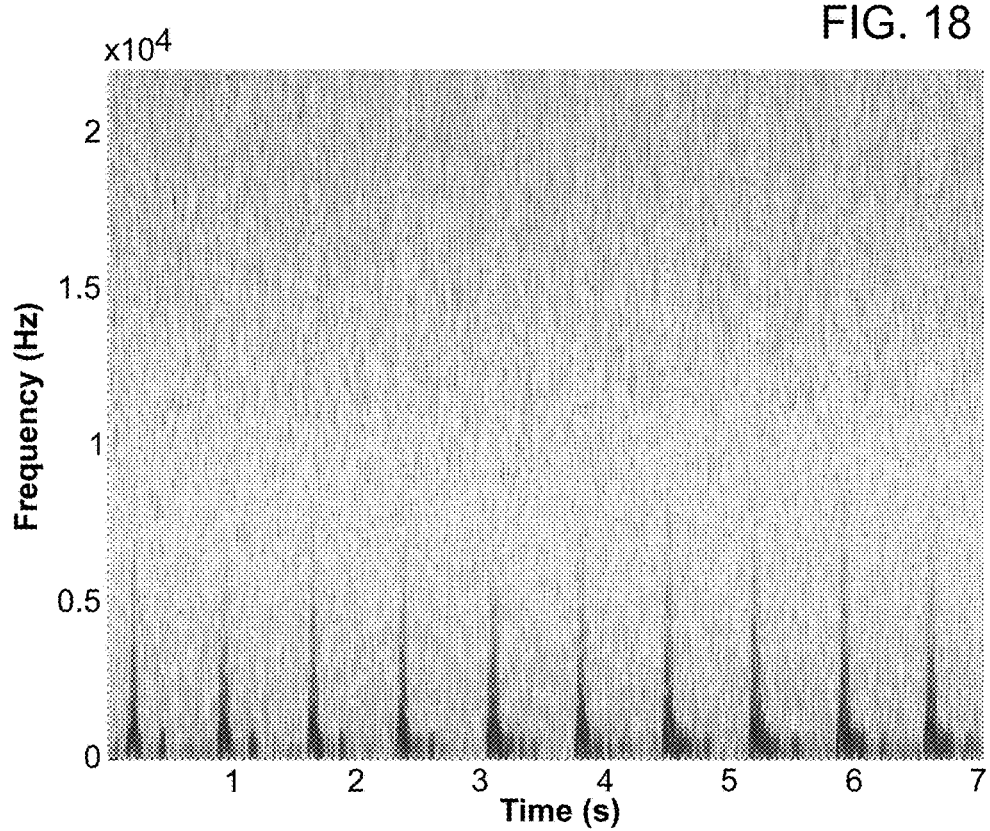

Each device also has an individual page containing a "Control Panel" for managing the device (FIG. 16). Here, the user can assign the device to a particular patient, as well as control the temperature and Doppler recording status. These changes are reflected in the column on the far right of the Control Panel, which displays the current status of each function (patient assignment, continuous temperature monitoring, continuous Doppler monitoring, and current Doppler monitoring).

It is necessary for the device to promptly alert clinicians of any problems developing with the flap. Alerts must quickly reach clinicians and provide actionable information. The device utilizes two different approaches for alerts. The first is a text message alert system to send a text message to the clinician's phone immediately following the detection of any problems such as a temperature discrepancy detected in the flap or the loss of certain characteristics of the Doppler signal. The second system is to log all alerts in the patient monitoring section of the web user interface. Alerts are color coded by priority and time stamped. Low priority alerts are simply time records of whenever recording is started or paused for whatever reason. High priority alerts are when the system detects an abnormality in the data being collected. The clinician will then know if the problem detected is related to the Doppler signal or the temperature probes. They can then check the web user interface for more information such as the graph of all the temperature probes for the patient or directly listen to the most recent Doppler recording or request another recording be taken to listen to. From this information the clinician can make the decision whether the patient will need a more thorough clinical examination or in some cases determine that the patient will need immediate revision surgery.

Measurements were conducted to test the longevity of ultrasound gel on the skin. A dime-sized amount of hypoallergenic ultrasound gel was applied to the skin and covered in a piece of plastic wrap. The plastic was secured to the skin with medical tape, ensuring that the gel was completely sealed against the skin. The "gel patch" was then worn over the next 24 hours to determine how long the gel would last before absorbing into the skin.

The presence of the gel under the plastic was checked every two hours and the results were recorded in a table detailing whether the gel was still present or not at the given time interval. It was found that the gel had been mostly absorbed into the skin after 8 hours of application, and completely absorbed into the skin after 9 hours.

Measurements were conducted to evaluate the performance of the Doppler ultrasound, temperature, and light monitoring functions of the device.

Participants were instructed to lay in the supine position in an examination chair. A standard blood pressure cuff was fixed around the participant's upper arm. Radial artery and cephalic vein signals were detected using Parks Medical flat Doppler probes. After confirming the quality of the signal at each placement location, the probes were taped in place against the skin using medical tape. Recordings were first collected from the radial artery. The cuff pressure was increased to the participant's systolic blood pressure (SBP) until there was a complete loss of arterial pulse, and a 5-second recording of the Doppler signal was collected. The cuff pressure was then decreased in increments of 20 mmHg to 0 mmHg and a 5-second recording was taken at each point. Cephalic vein recordings were done similarly from 40 mmHg down to 0 mmHg in increments of 10 mmHg with a 5-second recording at each point.

The spectrograms of these recordings for the first patient are depicted in FIGS. 17-24 to highlight the changing time-frequency components of these signals as occlusion increases. In the first recording shown in FIG. 17 with no occlusion it is possible to see the venous signal present in the low frequency range from 0 Hz to approximately 50 Hz across the duration of the recording, for example. A plurality of additional frequency bands can be used. Then the periodic spikes with each heart beat are the prominent feature of the arterial signal. At 20 mmHg (FIG. 18), it is possible to see this venous component becoming less pronounced.

Figure 19:
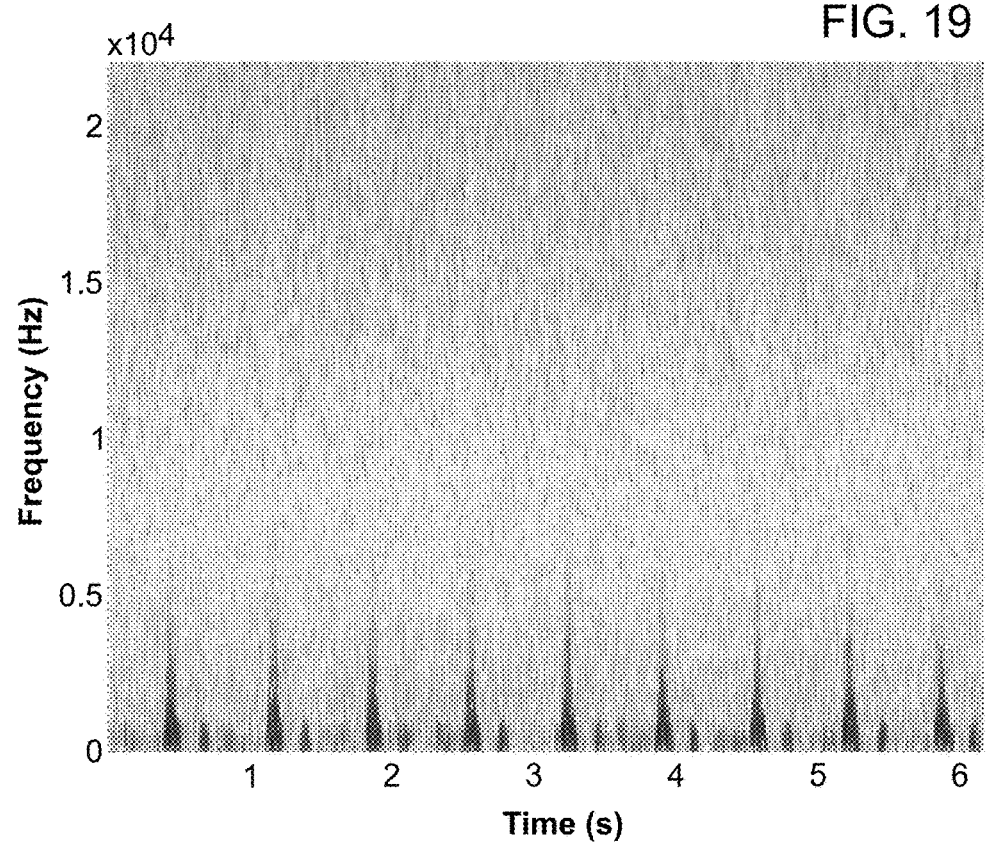
Figure 20:
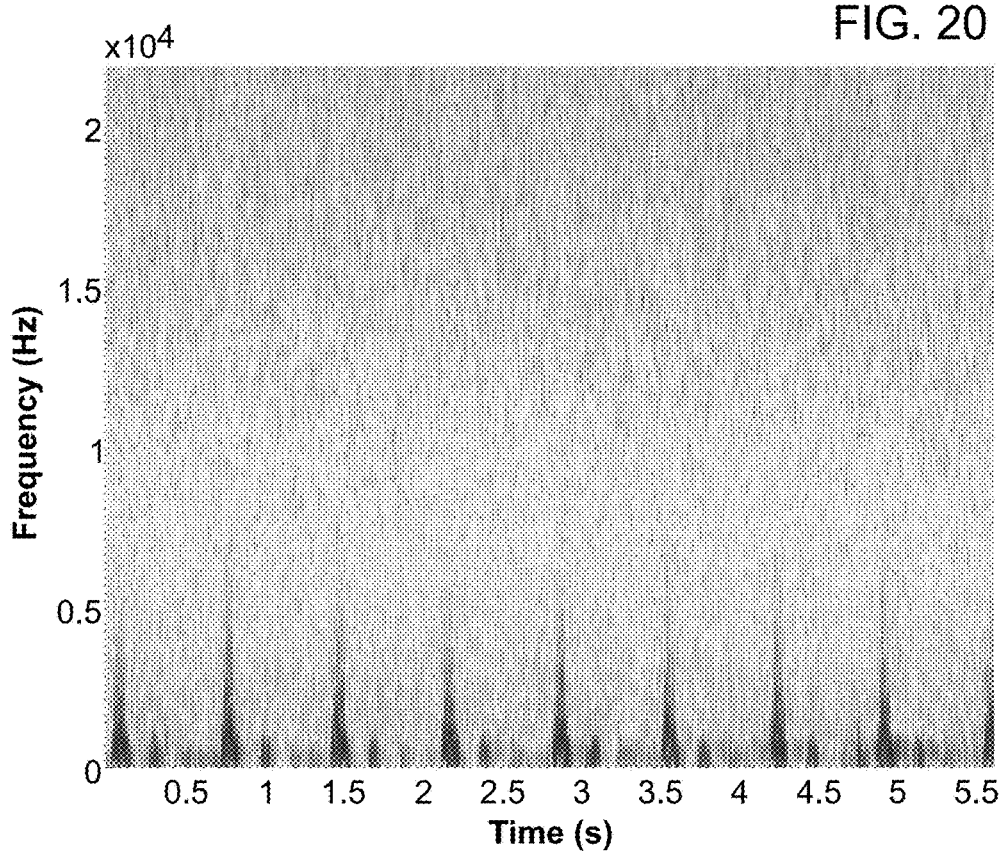

In FIGS. 19 and 20 the arterial signal is gone but it is still possible to see the triphasic component of the arterial signal as pressures have not yet gotten close to systolic blood pressure to impede arterial flow.

Figure 21:
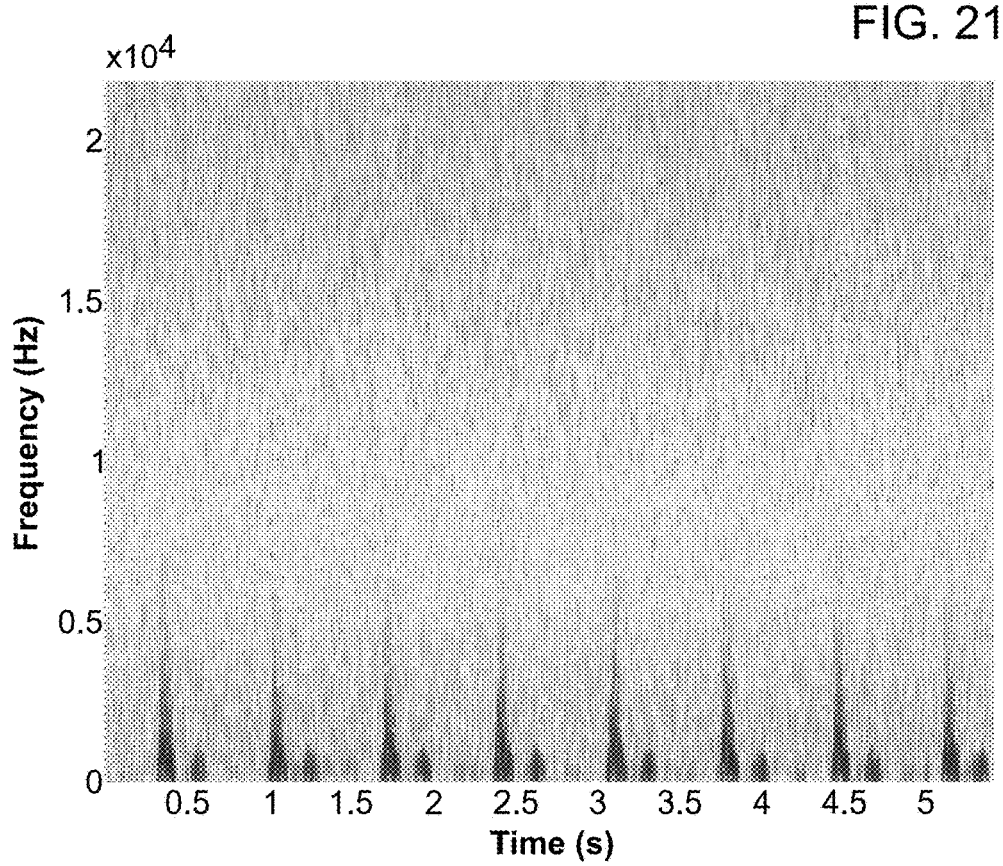
Figure 22:
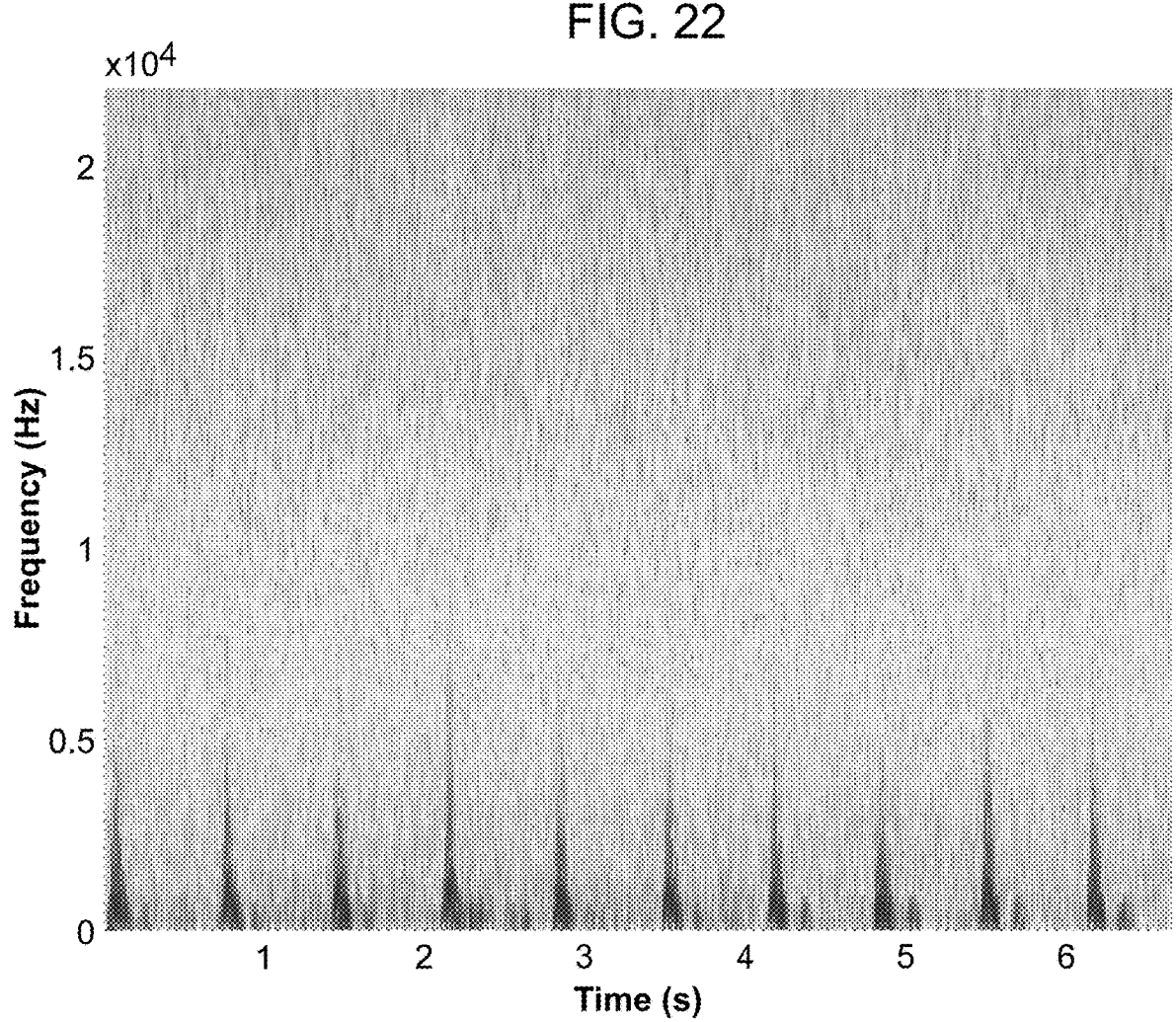

In FIGS. 21 and 22 the signal is biphasic still but only the first pulse is really pronounced as the arterial flow is being impeded by pressures nearing systolic blood pressure.

Figure 23:
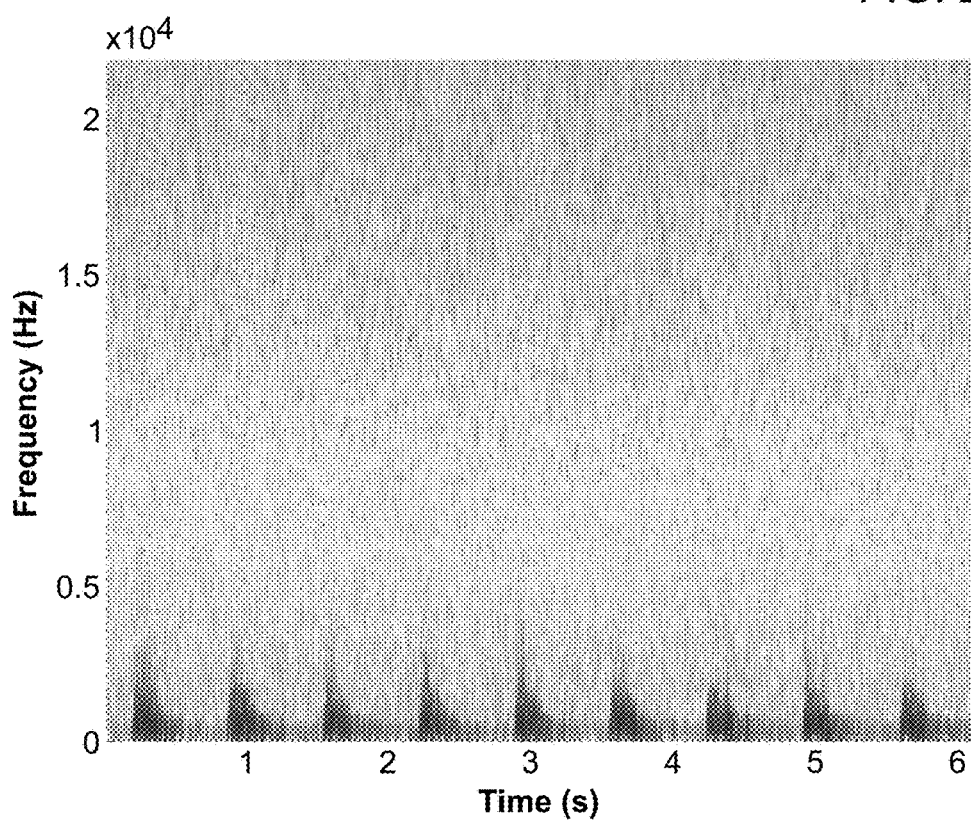
Figure 24:
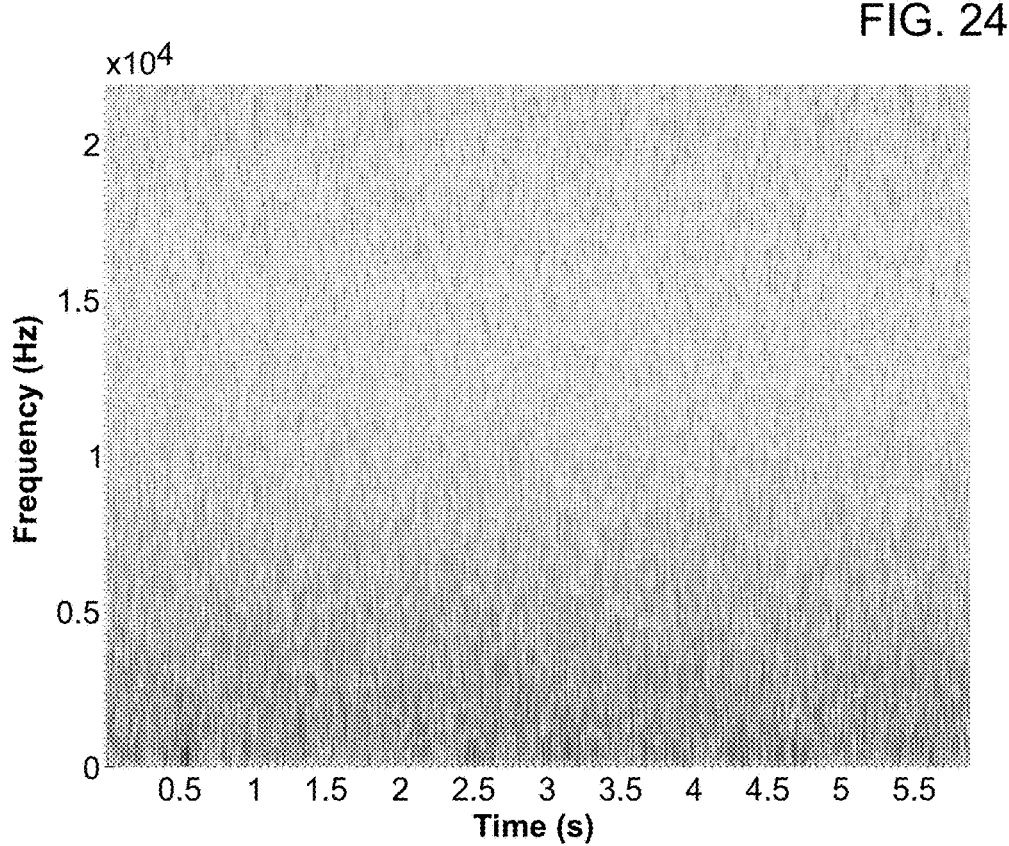

In FIGS. 23 and 24 it is evident that the flow is severely impeded. FIG. 23 still shows some flow where the signal is monophasic but the intensity of the peak is not as high in frequency as some of the less occluded signals. The frequency here corresponds to the velocity of the flow so a lower velocity flow is observed. In FIG. 24 the signal is completely lost at pressures above the total occlusion pressure.

Figure 25:
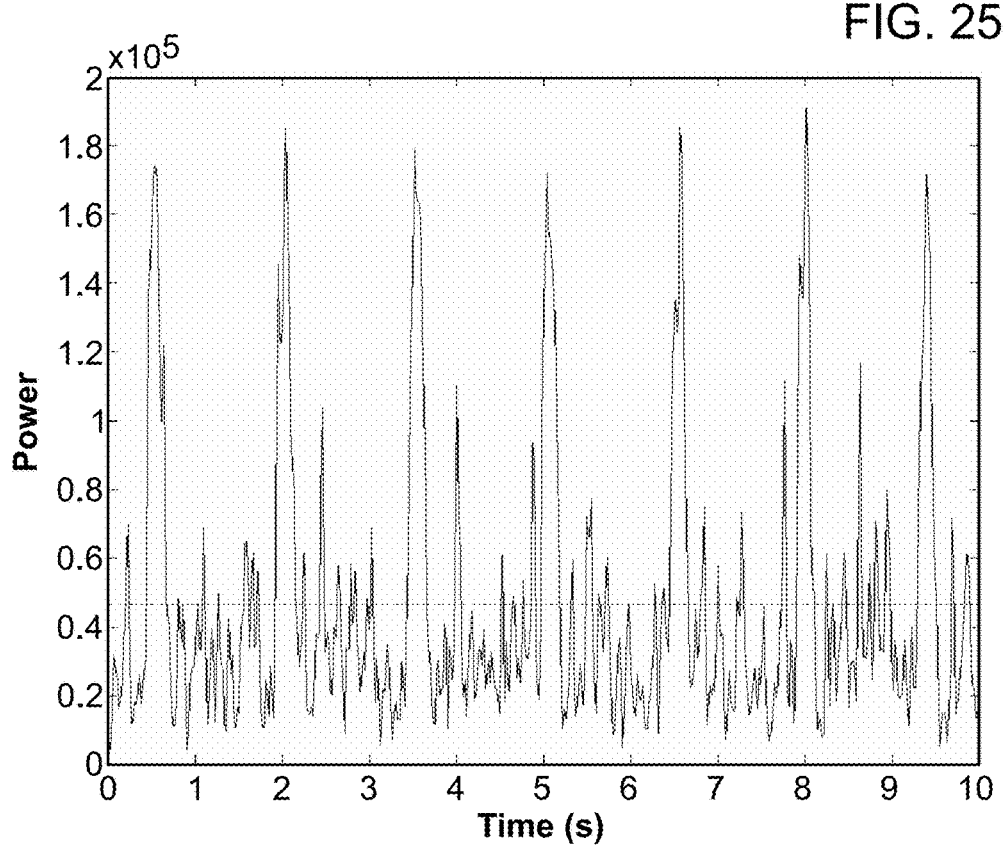
FIGS. 25-32 illustrate radial artery power window plots over time derived from ultrasound data collected at increasing levels of applied pressure between 0-140 mmHg by the system in accordance with embodiments described herein.
Figure 26:
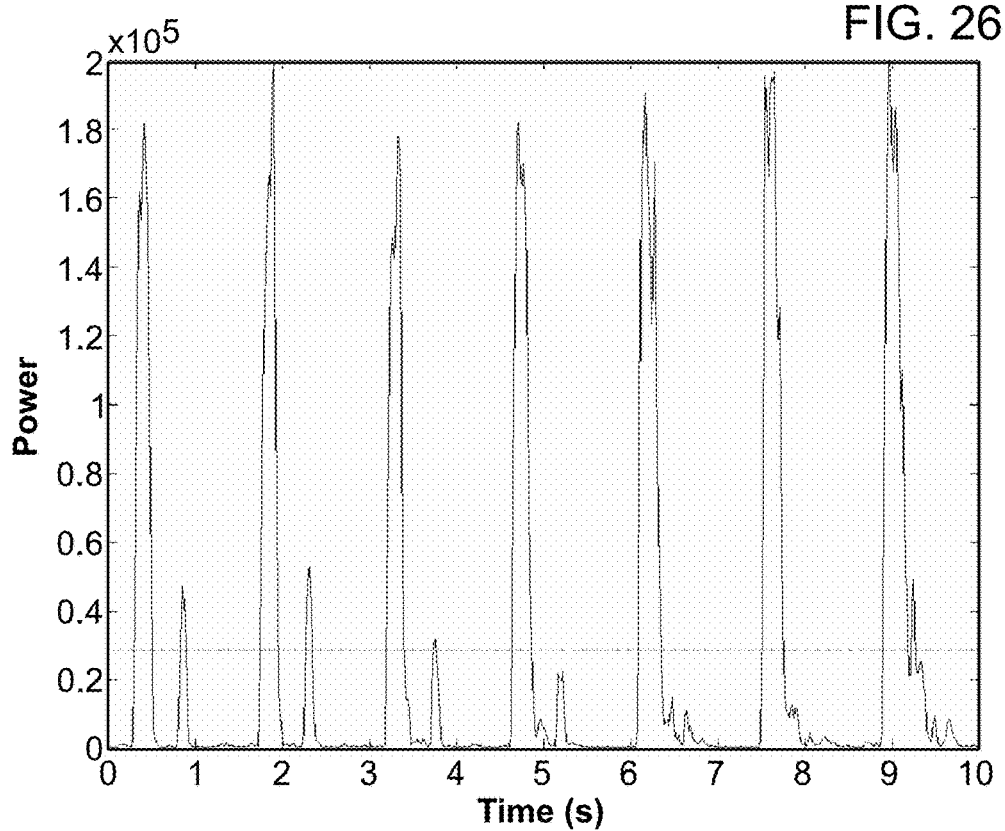

FIGS. 25-32 depict the power window signal computed for the same radial artery Doppler signals at varied levels of occlusion. In FIG. 25 it is possible to see both the prominent arterial pulses of the signal and the venous component of the signal depicted as a baseline greater than zero between arterial pulses. In FIG. 26, the cuff pressure has increased to 20 mmHg and the venous component of the signal is no longer present; however, the arterial pulses remain relatively unchanged.

Figure 27:
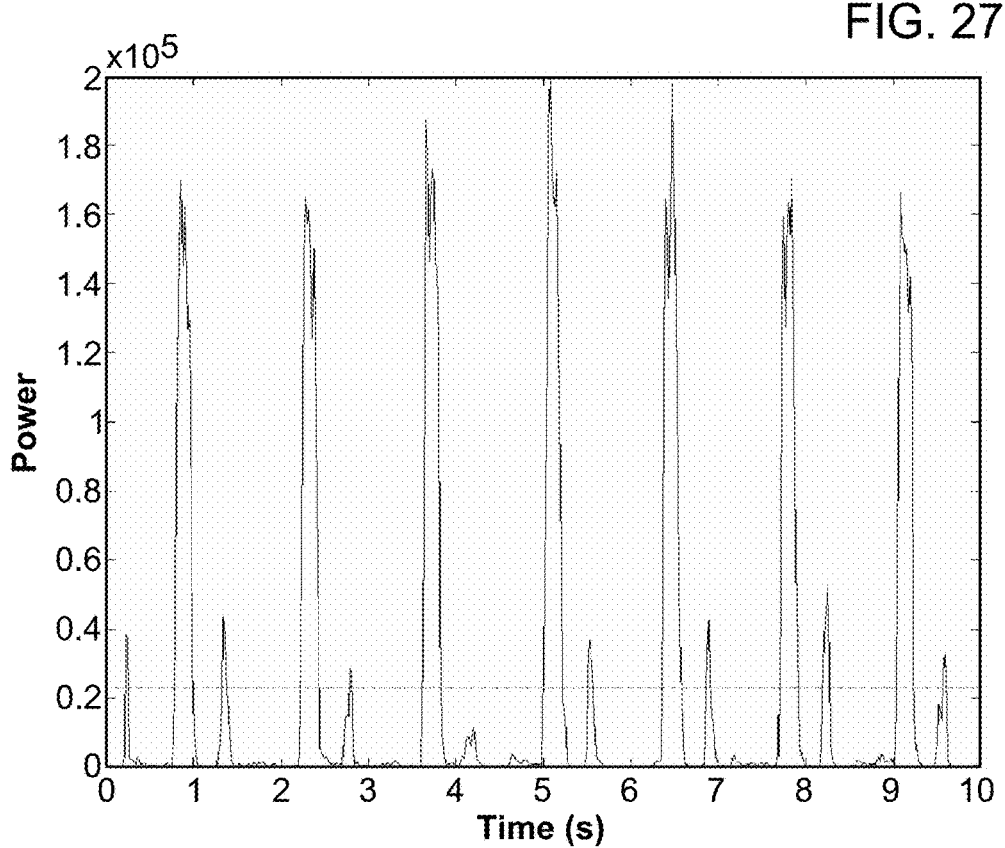
Figure 28:
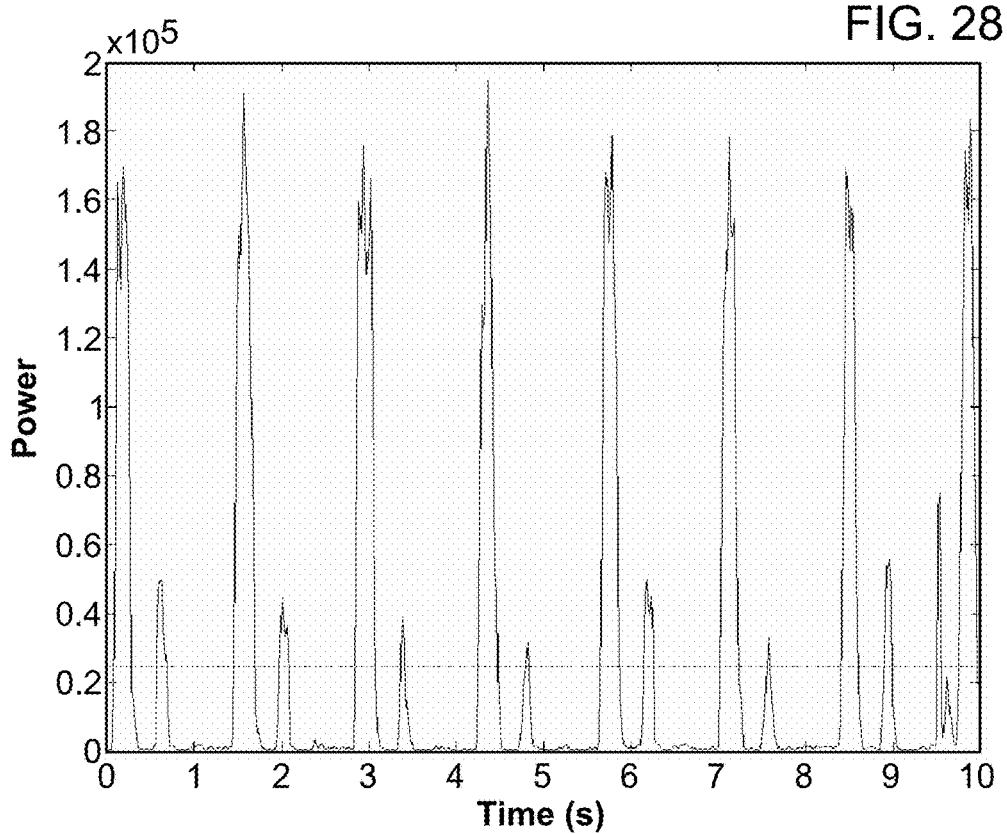
Figure 29:
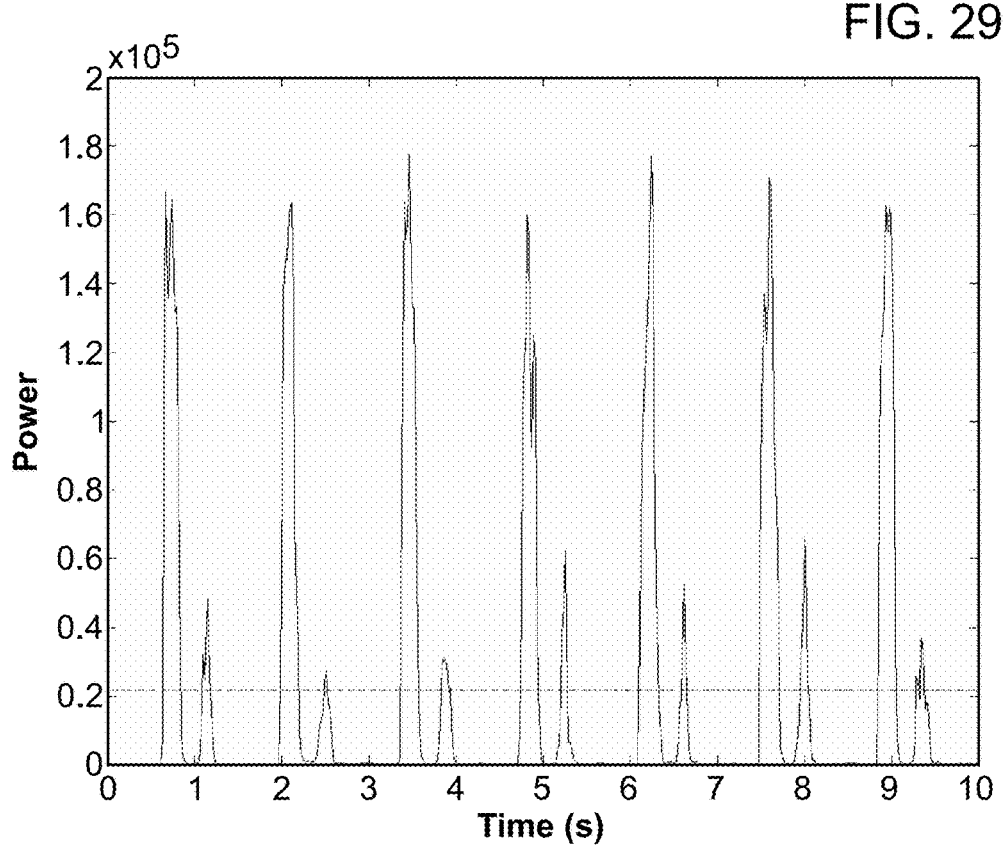
Figure 30:
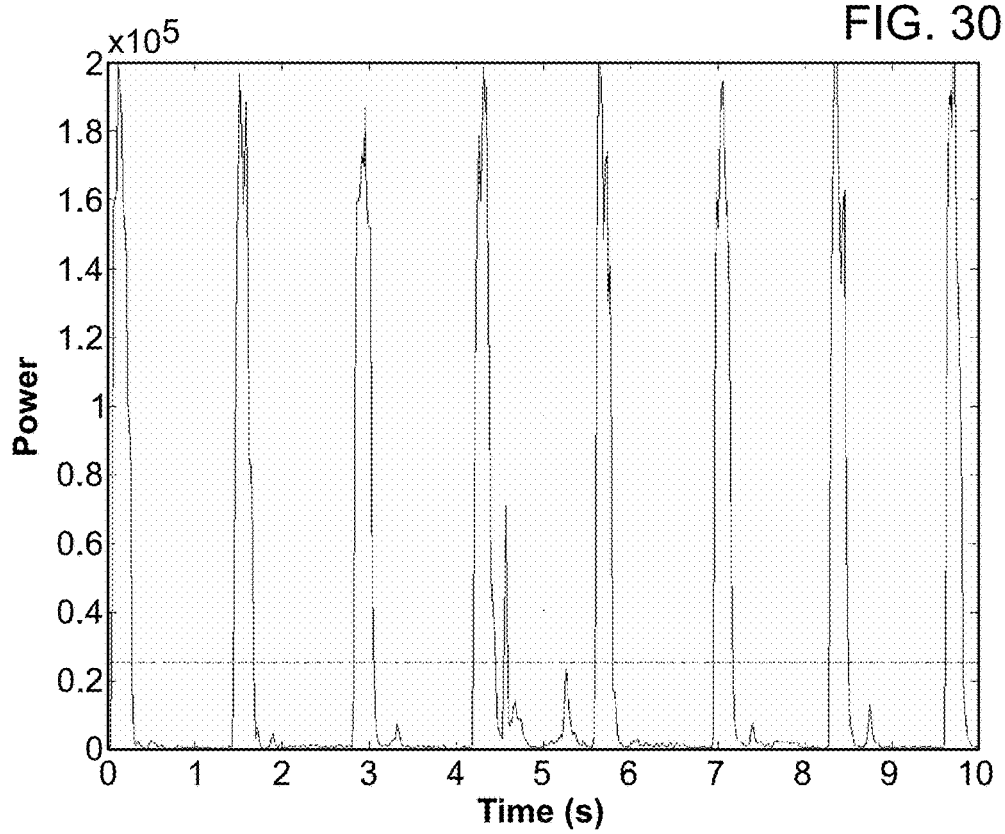

In FIGS. 27-29, the power window depicts the characteristic biphasic nature of the arterial signal at pressure levels from 40-80 mmHg. In FIG. 30, the signal clearly switches from biphasic to monophasic at 100 mmHg.

Figure 31:
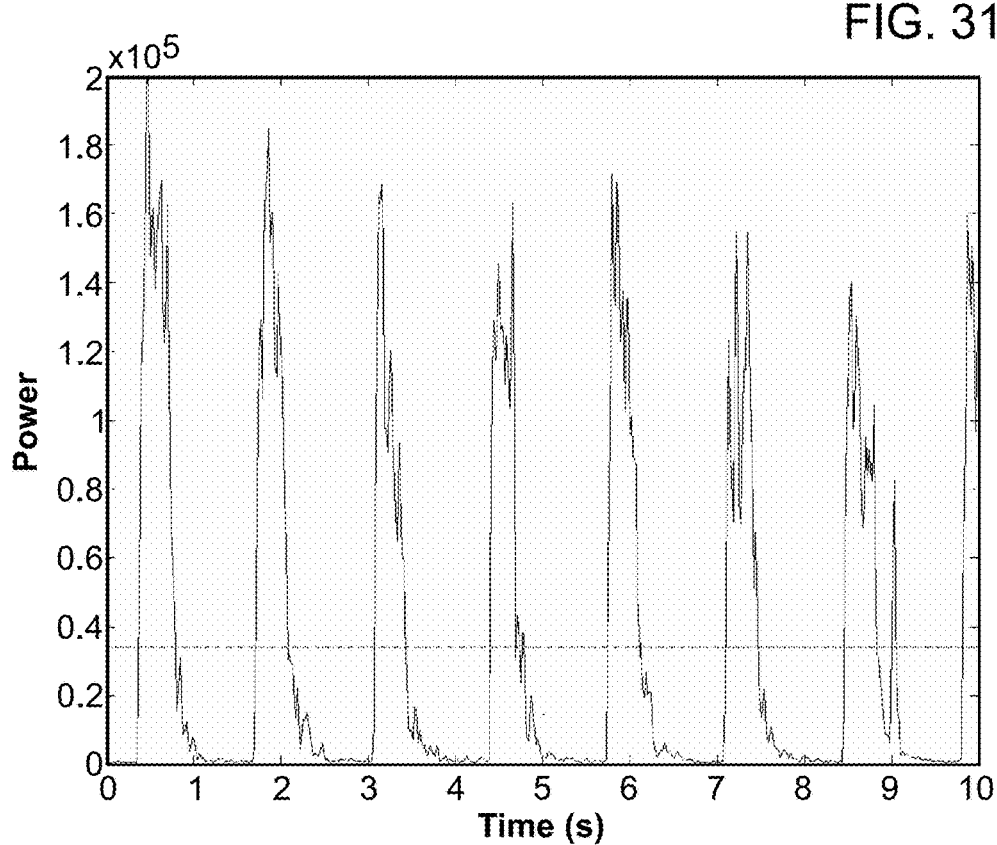
Figure 32:
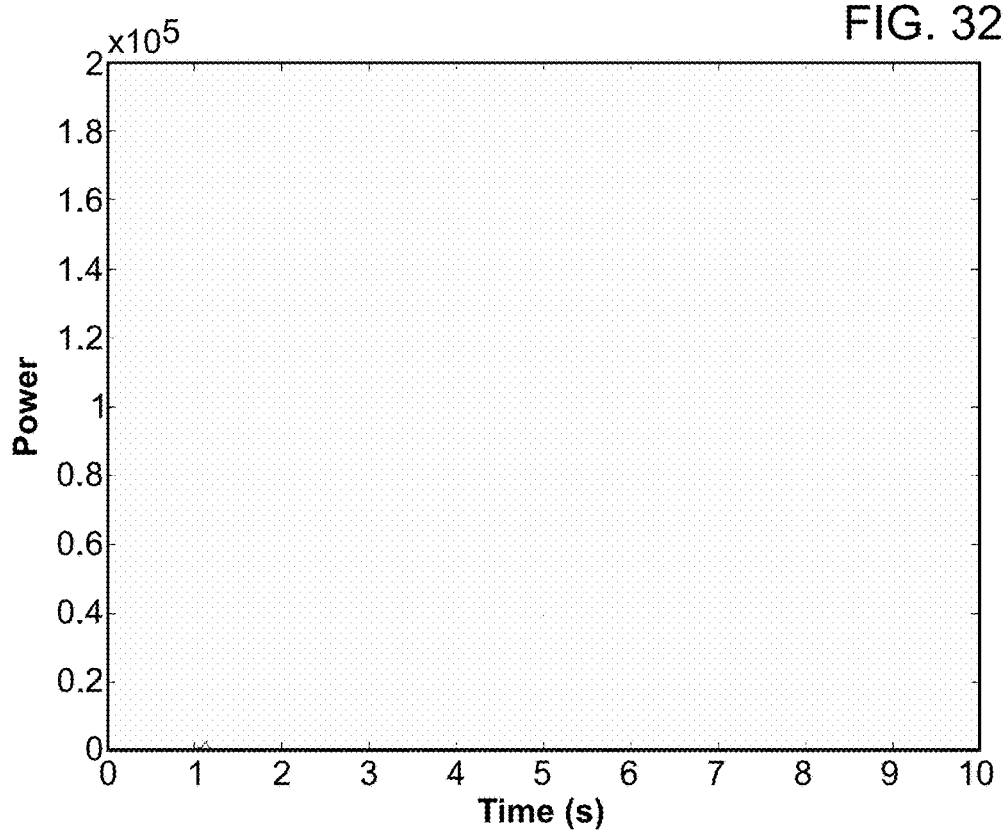

In FIG. 31, the signal is monophasic and the peak width has slightly increased. In FIG. 32, there is total occlusion and the signal is no longer visible on the same scale.

In order to monitor two probes from a single input of the Doppler flow meter, the system according to some embodiments described herein contains multiplexing circuitry comprising two DPDT-Relays controlled from digital output pin 6 on the Arduino via a current sinking transistor (see FIG. 34). The status of digital pin 6 allows the system to select between Flap Probe 1 or Flap Probe 2 when making recordings. Signals are recorded directly from the audio output of the Doppler flow meter through a Syba C-Media USB sound card interfacing with the Raspberry Pi.

Figure 36:
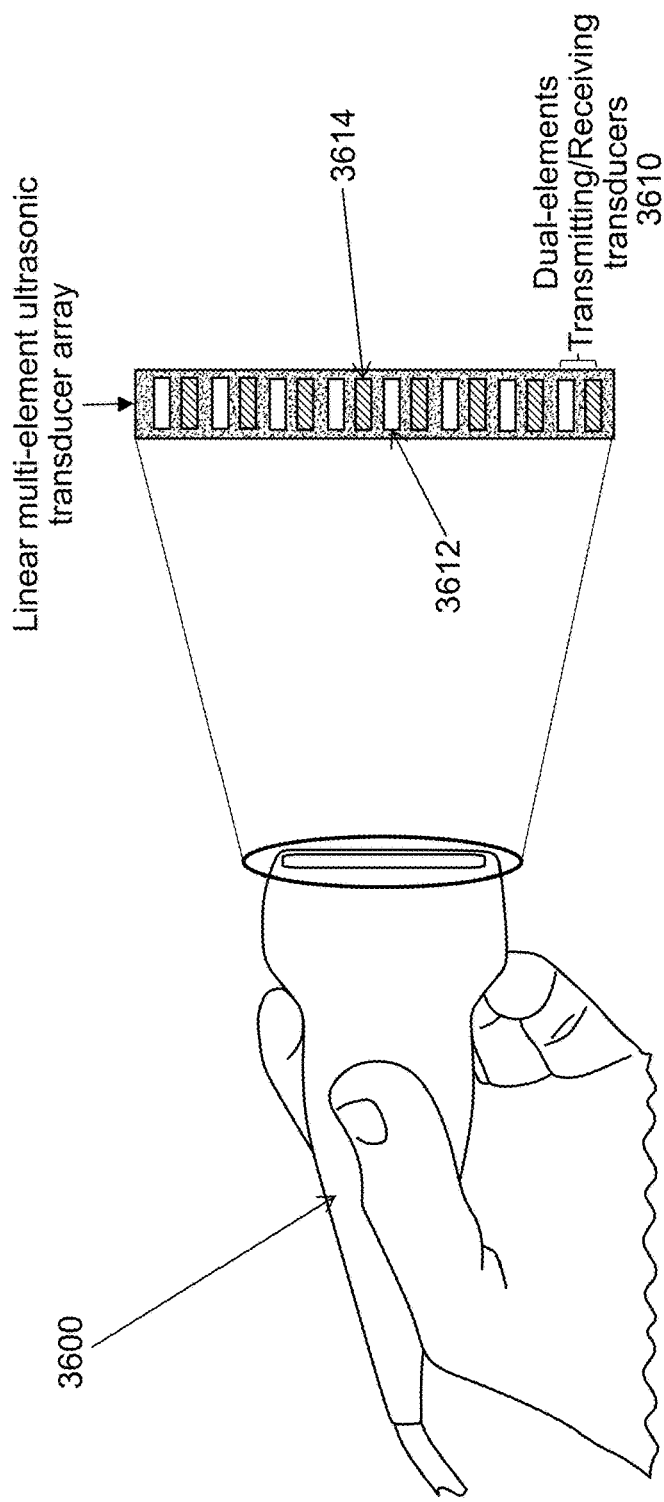
FIG. 36 illustrates portable handheld linear transducer array in accordance with embodiments of the invention.

In some embodiments, the probe holder 3600 can include Doppler ultrasound probes 20 in the form of a linear multi-element transducer array as shown in FIG. 36. The array can have pairs 3610 of alternating transmitting transducers 3612 and receiving transducers 3614. In alternative embodiments, the linear multi-element transducer array can be a non-imaging or imaging array. In embodiments where the linear transducer array is an imaging array, digital beamforming can be used to produce a low resolution image using pulsed transmission and beam steering techniques. In some embodiments, the linear multi-element transducer array can have 4, 8, 16, or up to 32 transducer elements. In some embodiments, each transducer element can be 3 to 7 mm on a side.

The device can accurately measure small differences in temperature between probes that are located on the transplanted tissue and those that are located as a reference on nearby healthy well perfused tissue. To verify that the probes reported the temperature within 0.1° C. agreement, extended recordings were taken with all four probes in a temperature controlled water bath at three different temperatures. Recording times were five minutes in duration and the bath was set to 34° C., 38° C., and 42° C.

Figure 35A:
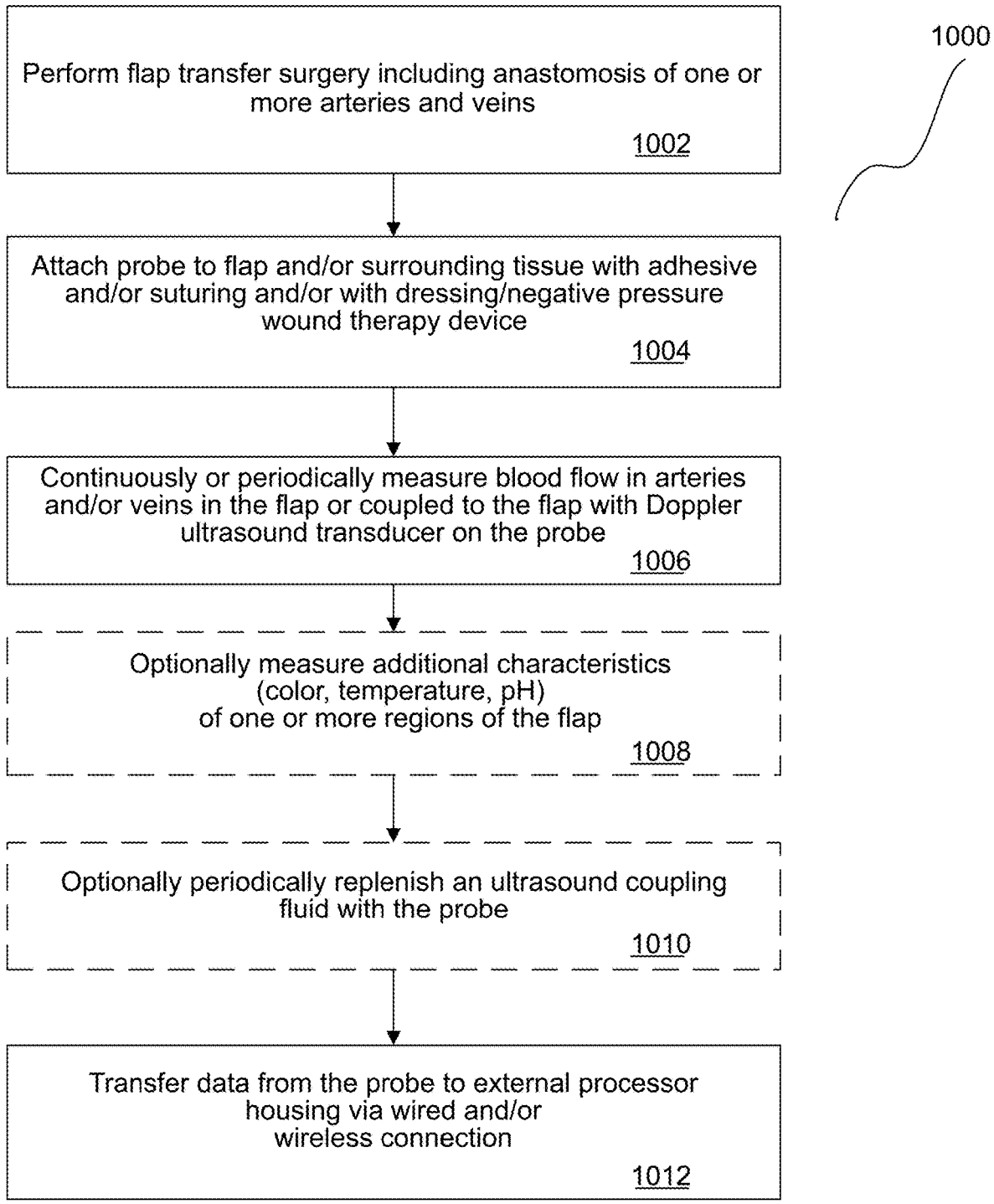
FIG. 35A illustrates a schematic for a method of measuring vascular deficiency in accordance with several embodiments of the present disclosure.
Figure 35B:
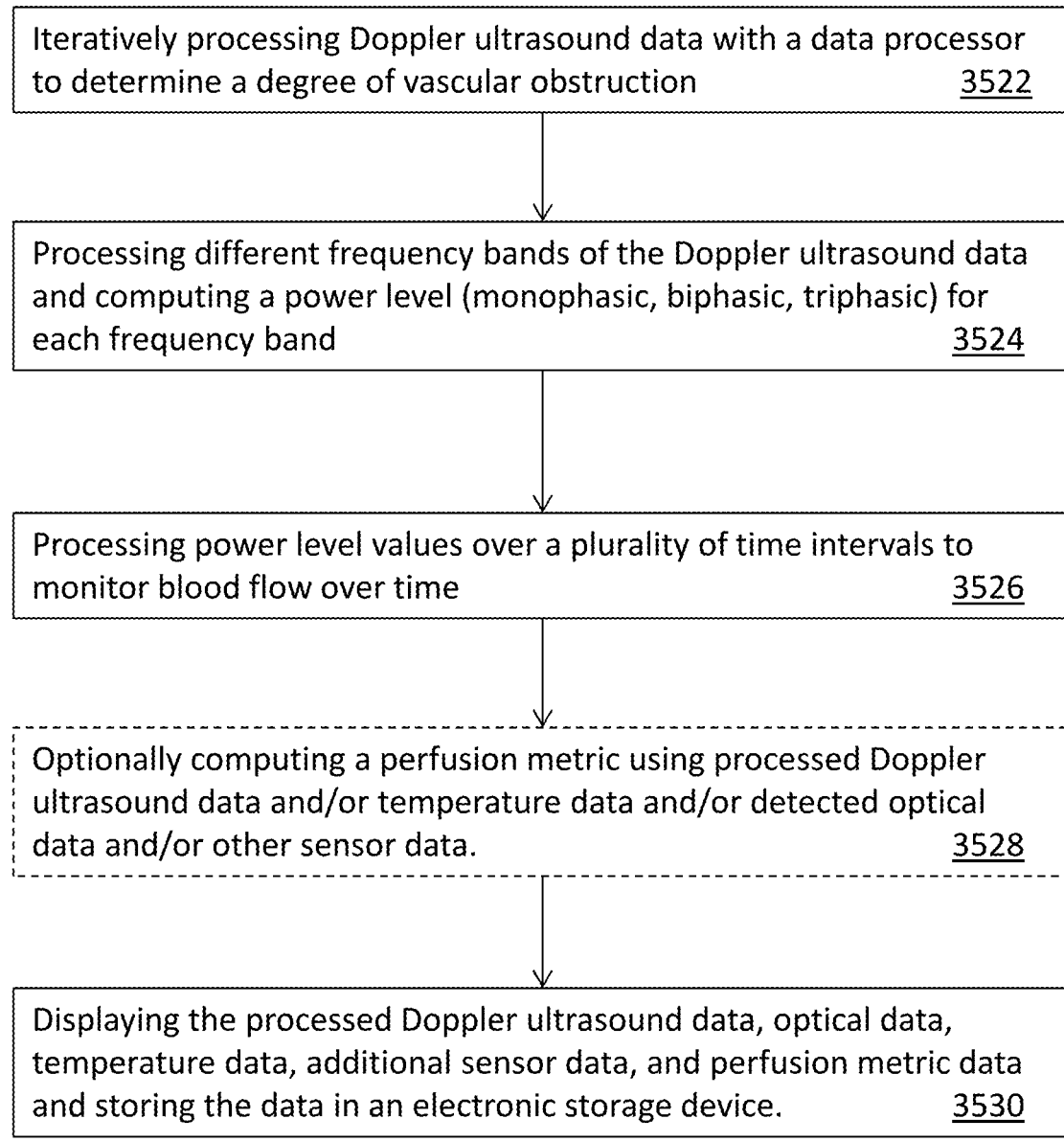
FIG. 35B illustrates a method for processing sensor data in accordance with embodiments of the invention.

The system can be operated by software stored in a system memory such as a non-volatile memory circuit device. The software operating functions are depicted in FIG. 35A, and data processing functions are described in FIG. 35B.

After tissue implant 1002, the probe is affixed to the skin 1004. Doppler data is acquired 1006 which can optionally include additional sensor data 1008. An ultrasound coupling fluid can be automatically or manually inserted on a periodic basis 1010. The data is transferred to an external processor 1012.

The data processor and/or associated logic circuits provide iterative analysis of the sensor data 3522. Different frequency bands or frequencies are periodically sampled 3524 and power level values computed 3526 as described herein. A perfusion metric is determined 3528 based on sensed data and the results displayed 3530.

Additionally, to ensure that the probes and their method of fixation to the patient was suitable for the thermistors to detect temperature changes on the surface of tissue consistent with varied degrees of perfusion, a similar study to that for the Doppler ultrasound verification was conducted. A subject was instructed to lie in the supine position with arms at their side. A blood pressure cuff was affixed to one arm. A temperature probe was placed on the proximal and distal forearm region of each arm so that live temperature recordings could be taken from the four probes simultaneously. The blood pressure cuff was then inflated to 20 mmHg and held there for a minute as temperature values were recorded once per second from each of the probes. The pressure was released and the temperature between the arms was allowed to equalize. Then this process was repeated by inflating the cuff to 40 mmHg, 60 mmHg, 80 mmHg, 100 mmHg, 120 mmHg, and 140 mmHg. One arm served as the tissue being tested with the pressure of the cuff being used to simulate different levels of venous and arterial occlusion. The other arm served as a location for the two reference probes.

Analog temperature signals are acquired from 100 k$\Omega$ NTC thermistors and digitized by an ADC on-board the Arduino controller with an 8-bit resolution for temperature recordings sensitive to 0.1° C. The temperature probes are also carefully calibrated for agreement across all four probes to 0.1° C. so that an accurate determination of the temperature differential between the transplant and surrounding tissue can be made.

The final holder for the combination Doppler-temperature probes was 3D printed from the design. The piece was printed from ABS plastic and fixed with the Doppler probe and thermistor. The ultrasound-gel catheter was also fixed in place in the holder.

The final case for an embodiment of the device was drawn in Solidworks and 3D printed. The case consists of two separate pieces that fit together to form a box around all of the components. The bottom piece of the case was developed to hold all of the circuitry in place, including spots for the Arduino, Raspberry Pi, and breadboard, for example.

The top piece of the case was printed with a series of holes for the jacks, switches, buttons, and lights. Additionally, a large space was left for the panel of the Doppler box. The top face of this piece of the case serves as a control panel for the user, containing all of the necessary components for managing the status of the device. Using these controls, the user can turn on monitoring for each of the probes, record an instant Doppler signal, and switch on the speaker of the Doppler box.

The website was developed for mobile in HTML5 with the Bootstrap framework (v3.3.6) and an additional CSS stylesheet for managing other stylistic aspects of the interface. A functional login system was developed that restricts access to registered members. This is managed by a user MYSQL table in the system database.

Figure 33:
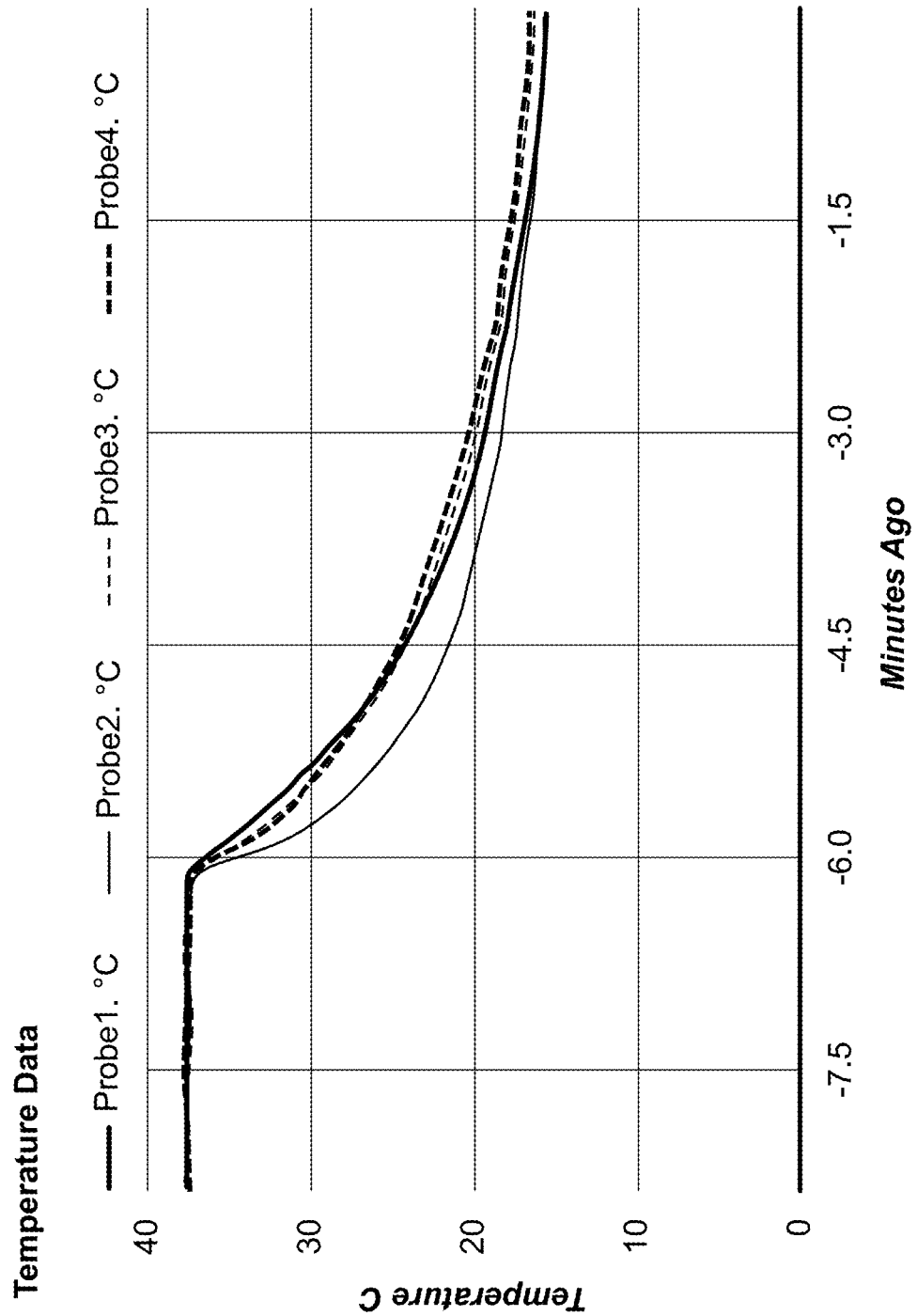
FIG. 33 illustrates example temperature data collected with probes and systems in accordance with embodiments described herein.

From the main portal, the user can access both patient and device information. The patients section of the application lists all of the patients currently enrolled in the system (which can be added and deleted from the database directly from the app). Each patient has a page associated with him or her that displays data from the device in real time. From this page, the user can access patient alerts, temperature graphs (FIG. 33), and Doppler ultrasound recordings that have remotely been uploaded to the interface via the device. Furthermore, the user can check the status of the device and control the system remotely from the app.

The coordination of the system is performed by a Raspberry Pi embedded computer. This unit coordinates the data collection polling sensors from the Arduino as well as making recordings of the Doppler signal through a USB sound card. The Raspberry Pi also performs the data analysis and generates alerts for a given patient and transmits data to the remote server to be accessible from the web application.

The device has been shown capable of continuous temperature monitoring over an extended period of time. Furthermore, these data are accessible from the user interface in real time. The website application has the capability of displaying data from numerous probes at a single time, allowing temperature readings from both individual and combination probes to be plotted on a single graph. This enables the surgeon to easily compare the temperature at the reference sites and on the flap surface to ensure they are consistent.

The device has also been shown capable of both continuous and immediate Doppler monitoring. The recordings are effectively uploaded to the server in realtime and organized by the patient from which they originate. The user can then immediately listen to the time-stamped recording directly from the user interface. This enables the surgeon to make decisions regarding the status of anastomosis without needing to be present at the patient's bedside or to rely on subjective descriptions of the Doppler signal from the clinician who performed the examination.

The use of the device in the ICU eliminates the need for hourly clinical examinations by nursing staff, thereby freeing up time for the staff to monitor other patients. By automating processes that were previously required to be completed manually by clinicians, hospitals could potentially save money in four ways: reduction of equipment, reduction of time spent in the ICU, reduction of staff, and reduction of overtime payment. While the latter two pose considerable ethical issues, from a financial standpoint the device would serve to benefit the hospital's budget. If such a system was capable of continuous, remote monitoring with minimal-to-no need for regular clinical examination, existing monitoring equipment such as bedside Doppler ultrasound components and supplemental flap monitoring systems could be replaced with a single, reusable device that effectively monitors multiple parameters at once. Furthermore, the portability of the device would enable patients to be transferred out of the ICU faster, thus saving the hospital costs associated with ICU-based care.

The device can reduce out-of-pocket payments from patients who spend time recovering in the ICU. Although there will be significant variation in these costs from person-to-person, a reduction of time spent in the ICU will directly correspond to a decrease in costs for ICU-based care. Similarly, insurance companies would see a reduction in costs for the patient's visit at the hospital.

The device and its components are intended for multiple uses. All probes and probe-holders can be sterilized in an autoclave after clinical use and reused on the next patient. This significantly reduces the waste that would be produced if the components were designed for one-time use. Furthermore, the Doppler unit is powered by a rechargeable battery, thereby reducing the waste that would be generated by a single-use battery component. It should be noted, however, that this rechargeable lithium battery should be recycled at the end of its life cycle in order to minimize the impact on the environment. Over the entirety of its lifetime, the device will produce a minimal amount of waste, most of which can be recycled.

The device provides patients and clinicians with an improved system for postoperative monitoring in microvascular free tissue transfer. As such, it is absolutely necessary that the device is safe for all users. The device is designed to improve the quality of care for patients who are recovering from surgery. The objective is not only to meet current monitoring standards that are in place at hospitals, but to exceed these without compromising patient safety. Proper measures have been taken to ensure that the device meets the safety requirements that are in place for medical devices of this nature.

The device reuses materials used to develop the device are readily accessible and could be reproduced either manually or automatedly with the appropriate preparation. The device case could be 3D printed from the existing design file, along with the probe holders. Or the file could be used to make a mould for mass produced and low cost injection moulding. The device components (such as circuitry, switches, buttons, lights, etc.) could be purchased in bulk and assembled in the case using the same techniques that were implemented for the original device. Furthermore, the Doppler, temperature, and color-sensor probes can be purchased in bulk and wired to interface with the device. This may require some modification so that the plugs will be compatible with the jacks on the device case, but it is achievable using the original device as a guideline. Ultimately, the physical aspects of the device could be reproduced, either individually or in bulk.

The described system continuously monitors temperature, Doppler ultrasound and color in subjects for the duration of their recovery. It is an improvement upon the already established practice of observing these physiological parameters by monitoring them continuously, objectively, and with a higher degree of sensitivity. Through signal processing methods, the device is capable of alerting clinicians, via SMS or visual alerts on the web interface, to potential complications even during periods of time between the hourly checks typically performed by a nurse. By checking for the presence of a non-zero baseline of the Doppler ultrasound power signal, the device can determine venous status, and by checking for the presence of the secondary peaks the device can determine arterial perfusion status. Furthermore, the device can detect surface temperature fluctuations to 0.1° C. and distinguish between possible venous or arterial complication using the aforementioned criteria from literature regarding temperature.

An additional benefit is that the data recorded to the web based application makes it feasible to remotely inform clinicians regarding the status of a patient and provides a record of the Doppler signals and temperature of the transplant that can later be referred to. Previously, Doppler signals were evaluated audibly and subjectively and no recording existed to be referred to. In several cases when a physician had to make a determination as to whether the transplant required revision surgery, only second hand descriptions of the Doppler signal from other clinicians who had been performing the monitoring were available.

Because the end result of the acquired signals will involve digitizing them regardless and allowing surgeons to hear them remotely, the Doppler housing will include small and efficient integrated circuits for Doppler ultrasound front end modules. This provides miniaturization of the associated circuitry and allows for a miniature device to be worn on the patient and interface with the sensors and transmit that over bluetooth or wireless to a base unit that performs the signal processing and communication with the remote server.

For further miniaturization, custom Doppler probes can be manufactured so that the piezo crystals responsible for transmitting and receiving the ultrasonic signals were built directly into the probe case design. The possibility to 3D print objects with electrical conduits makes this a promising option and then the light sensor could also be integrated into the very same probe holder along with its associated circuitry and then a single cable could connect the three transducers to whatever unit was responsible for acquiring the data.

For signal processing, the collection of much more data over a large population of patients over the course of using this device would allow for the refinements of the signal processing algorithms and possibly even new discoveries being made about the relationships between Doppler, temperature, and color and their early prediction of the loss of flap perfusion. These improved algorithms should continue to be incorporated into the device. It is possible to visualize the Doppler signal and use it to get a visual representation of the velocity profile of blood travelling through the vessels.

The following claims encompass numerous modifications or equivalents of the various embodiments described above without departing from the scope of the present invention.

What is claimed is:

1. An ultrasound device for monitoring a surgical flap of vascular tissue, comprising:
   an epidermal probe that detects one or more physiological characteristics of a surgically transplanted tissue flap, the tissue flap comprising a section of tissue having a tissue flap blood vessel anastomosis to a blood vessel in tissue that is adjacent to the tissue flap and wherein the tissue flap includes arterial blood flow and venous blood flow, the epidermal probe including a Doppler ultrasound transducer configured to be positioned on a surface of the tissue flap that at least periodically in response to control signals from a controller, transmits ultrasound signals into the tissue flap at a plurality of frequencies, and thereby automatically detects ultrasound signals from within the tissue flap to generate detected ultrasound data, the detected ultrasound data including both a first detected ultrasound signal that measures the arterial blood flow and a second detected ultrasound signal that measures the venous blood flow;
a data processor communicatively connected to the Doppler ultrasound transducer and configured to automatically and iteratively process the detected ultrasound data periodically received from the epidermal probe at each of the plurality of frequencies to determine a tissue flap condition indicative of at least one of reduced arterial blood flow or reduced venous flow in the tissue flap; and
a display communicatively connected to the data processor that displays the tissue flap arterial blood flow condition and the tissue flap venous blood flow condition with a graphical user interface.

2. The device of claim 1 wherein the epidermal probe is configured to be attached to the surface of the tissue flap and the data processor computes arterial and venous blood flows to determine a level of flap perfusion.

3. The device of claim 1 wherein the probe comprises a temperature sensor that generates flap temperature data such that the data processor compares a temperature of the flap with a temperature of reference tissue to detect a temperature differential.

4. The device of claim 1 wherein the controller controls transmission of the ultrasound signals into the tissue flap at the plurality of frequencies including a first frequency to measure a first blood flow velocity in a first range, the Doppler ultrasound transducer having 16 or less transducer elements.

5. The device of claim 4 wherein the controller controls transmission at a second frequency higher than the first frequency to measure a second blood flow velocity in a second range.

6. The device of claim 4 wherein the controller is configured to control continuous wave ultrasound signals that are transmitted into the tissue flap with a first transducer element and wherein the Doppler ultrasound transducer detects the first and second ultrasound signals with a second transducer element.

7. The device of claim 1 wherein the probe includes a light sensor and a light source.

8. The device of claim 7 wherein the light sensor comprises a first photodetector and a second photodetector.

9. The device of claim 7 wherein the light source comprises one or more light emitting diodes (LEDs).

10. The device of claim 7 wherein the light sensor generates detected optical data to measure at least one of the arterial blood flow and the venous blood flow in the tissue flap.

11. The device of claim 10 wherein the epidural probe comprises a first epidural flap probe and a second epidural flap probe to generate Doppler data in different regions of the transplanted tissue flap and wherein the data processor is configured to:
receive the Doppler data and the detected optical data;
compute a perfusion metric based thereon;
compare the computed perfusion metric to a reference threshold value; and
transmit an indicator of the tissue condition.

12. The device of claim 7 wherein the light sensor comprises an imaging device having a two-dimensional array of at least 100,000 pixels.

13. The device of claim 7 wherein the light sensor measures a blood volume or pulsatile blood volume in the tissue flap.

14. The device of claim 1 wherein the probe is configured to be affixed to the tissue flap with a suture or an adhesive.

15. The device of claim 1 wherein the ultrasound transducer comprises a non-imaging transducer.

16. The device of claim 1 wherein the data processor receives Doppler velocity data in response to a plurality of different frequency bands of a transmitted continuous wave signal.

17. The device of claim 1 wherein the probe is connected by a cable to a body-worn processor housing.

18. The device of claim 17 wherein the body-worn processor housing comprises the data processor, the controller, a battery, and a wireless transmitter, the wireless transmitter being configured to transmit the ultrasound data to at least one of the display positioned in a display and processing unit or an external network server.

19. The device of claim 1 wherein the device comprises a fluid delivery tube outlet to provide an ultrasound coupling fluid between the surface of the tissue flap and the ultrasound transducer.

20. The device of claim 19 wherein the fluid delivery tube outlet is on a probe housing of the epidermal probe such that the ultrasound coupling fluid is delivered from a fluid source.

21. The device of claim 20 wherein the fluid source is mounted within a body-worn processor housing and is fluidically coupled to the probe with a tube through a cable and further comprising a manual pump and/or an electrical pump to move the coupling fluid through the tube outlet.

22. A method of post-surgical tissue monitoring, comprising:
affixing an epidermal probe at a surgical site on a surface of skin of a transplanted tissue flap that detects at least periodically one or more physiological characteristics of the tissue flap wherein the tissue flap is connected to adjacent tissue with a blood vessel anastomosis, the epidermal probe having at least one ultrasound transducer being connected to a controller configured to transmit ultrasound signals at a plurality of frequencies into the transplanted tissue flap, the transplanted tissue flap including arterial blood flow and venous blood flow such that detected ultrasound signals are thereby automatically measured with the at least one ultrasound transducer to generate detected ultrasound Doppler data;
receiving, by an interface to a monitoring logic circuit that is responsive to the epidermal probe, detected physiological data including at least the ultrasound Doppler data;
analyzing, in an automated, iterative process, the detected physiological data with a data processor to determine a tissue condition indicative of reduced vascular flow in the transplanted tissue flap, the detected physiological data including ultrasound Doppler data of the arterial blood flow and the venous blood flow in the transplanted tissue flap; and
displaying the tissue condition on a display with a graphical user interface, the display indicating a level of arterial blood flow and venous blood flow in the transplanted tissue flap during a monitoring period.

23. The method of claim 22 further comprises detecting temperature data and wherein the analyzing further includes determining, with the data processor, at least one of the arterial blood flow or the venous blood flow to detect a level of flap perfusion, and includes comparing a temperature of the tissue flap with a temperature of reference tissue to detect a temperature differential.

24. The method of claim 22 further comprising controlling transmission of the ultrasound signals into the tissue flap at the plurality of frequencies including a first frequency to measure a first blood flow velocity in a first range and controlling transmission at a second frequency higher than the first frequency to measure a second blood flow velocity in a second range.

25. The method of claim 22 further comprising transmitting and detecting the ultrasound signals with a transducer assembly in the probe and wherein continuous wave ultrasound signals are transmitted into the tissue flap with a first transducer element and the detected ultrasound signals are detected with a second transducer element.

26. The method of claim 22 wherein the probe includes a light sensor and a light source wherein the light sensor comprises a first photodetector and a second photodetector and wherein the light source comprises a light emitting diode (LED), the light sensor generating detected optical data to measure at least one of the arterial blood flow and the venous blood flow in the tissue flap.

27. A method of measuring vascular deficiency, comprising:
measuring temperature of a transplanted tissue flap on a patient with a temperature sensor to generate temperature data;
positioning a Doppler ultrasound probe on a skin surface of the transplanted tissue flap of the patient to at least periodically measure an arterial blood flow level and a venous blood flow level in the transplanted tissue flap of the patient over a period of time, the Doppler ultrasound probe being connected to a controller configured to transmit ultrasound signals at a plurality of different frequencies;
receiving, by an interface to monitoring logic circuitry responsive to detected Doppler ultrasound signals, blood flow velocity data obtained at the plurality of different frequencies;
analyzing, in an automated, iterative process, the received blood flow velocity data and the temperature data with a data processor to determine at least one of the arterial blood flow velocity level and the venous blood flow velocity level during the period of time; and
displaying the temperature data, the arterial blood flow velocity level and the venous blood flow velocity level on a display using a graphical user interface to determine a condition of the transplanted tissue flap.

28. The method of claim 27 wherein the analyzing further includes determining blood flow to diagnose a deep vein thrombosis (DVT) and determining whether the blood flow is monophasic or biphasic.

29. The method of claim 27 wherein the probe comprises a non-imaging transducer array having 16 transducer elements or less and further comprising performing a compression measurement to determine a presence of deep vein thrombosis (DVT).

30. The method of claim 27 wherein the step of measuring temperature with the temperature sensor comprises measuring the temperature with a thermistor that is configured to contact the tissue flap.

31. The method of claim 27 wherein the temperature sensor is mounted to the Doppler ultrasound probe.

32. The method of claim 27 wherein the step of measuring temperature with the temperature sensor comprises measuring the temperature with a light detector.

33. The method of claim 27 further comprising measuring the temperature with a thermal imaging sensor.

34. The method of claim 27 wherein the temperature data is measured at a first location on the tissue flap and at a second different location on the tissue flap.

35. The method of claim 27 further comprising detecting a color of the tissue flap with a light detector.

* * * * *